(12) United States Patent
Kalpin et al.

(10) Patent No.: US 9,339,601 B2
(45) Date of Patent: May 17, 2016

(54) METHOD AND APPARATUS FOR GUIDING AN EXTERNAL NEEDLE TO AN IMPLANTABLE DEVICE

(75) Inventors: Scott L. Kalpin, Harris, MN (US); Andrew Bzostek, Erie, CO (US); Steven L. Hartmann, Superior, CO (US); Matthew W. Koenig, Dacono, CO (US); Brad Jacobsen, Erie, CO (US); Scott A. Sarkinen, Greenfield, MN (US); Peter J. Borowitz, Spring Lake Park, MN (US); Bradley A. Jascob, Broomfield, CO (US)

(73) Assignee: Medtronic, Inc., Minneapolis, MN (US)

( * ) Notice: Subject to any disclaimer, the term of this patent is extended or adjusted under 35 U.S.C. 154(b) by 126 days.

(21) Appl. No.: 13/045,684

(22) Filed: Mar. 11, 2011

(65) Prior Publication Data
US 2011/0237936 A1  Sep. 29, 2011

Related U.S. Application Data

(60) Provisional application No. 61/317,563, filed on Mar. 25, 2010.

(51) Int. Cl.
*A61B 19/00* (2006.01)
*A61M 5/32* (2006.01)
*A61M 5/142* (2006.01)
(Continued)

(52) U.S. Cl.
CPC ........ *A61M 5/14276* (2013.01); *A61B 19/5244* (2013.01); *A61M 5/427* (2013.01); *A61B 19/201* (2013.01); *A61B 19/56* (2013.01); *A61B 2019/4857* (2013.01); *A61B 2019/5251* (2013.01); *A61B 2019/5458* (2013.01);
(Continued)

(58) Field of Classification Search
CPC .. A61B 19/201; A61B 19/5244; A61B 19/56; A61B 2019/4857; A61B 2019/5251; A61B 2019/5458; A61M 5/14276; A61M 5/427; A61M 2039/0081; A61M 2039/0238
USPC ........ 600/423, 426, 424; 604/288.04, 288.01, 604/116
See application file for complete search history.

(56) References Cited

U.S. PATENT DOCUMENTS 3,760,811 A  9/1973 Andrew
4,476,869 A  10/1984 Bihn
(Continued)

FOREIGN PATENT DOCUMENTS

EP  0723783 A1  7/1996
EP  0910300 A1  4/1999
(Continued)

OTHER PUBLICATIONS

International Search Report and Written Opinion mailed Sep. 13, 2011 for PCT/US2011/028918, which claims benefit of U.S. Appl. No. 13/045,686, filed Mar. 11, 2011.
(Continued)

*Primary Examiner* — Long V Le
*Assistant Examiner* — Colin T Sakamoto
(74) *Attorney, Agent, or Firm* — Harness, Dickey & Pierce, P.L.C.

(57) ABSTRACT

A support tool or a supply assembly that delivers a functional fluid to a patient includes an antenna array for receiving or sensing a navigation field. The navigation field can be generated from a localizer. The localizer can be incorporated or included in an implanted device.

29 Claims, 16 Drawing Sheets

(51) Int. Cl.
*A61M 5/42* (2006.01)
*A61M 39/00* (2006.01)
*A61M 39/02* (2006.01)

(52) U.S. Cl.
CPC ............... *A61M2039/0081* (2013.01); *A61M 2039/0238* (2013.01)

(56) References Cited

U.S. PATENT DOCUMENTS

| | | | |
|---|---|---|---|
| 4,804,054 A | 2/1989 | Howson et al. | |
| 4,905,698 A | 3/1990 | Strohl, Jr. et al. | |
| 5,006,115 A | 4/1991 | McDonald | |
| 5,009,644 A | 4/1991 | McDonald | |
| 5,080,104 A | 1/1992 | Marks et al. | |
| 5,099,845 A * | 3/1992 | Besz et al. | 600/424 |
| 5,171,228 A | 12/1992 | McDonald | |
| 5,201,715 A | 4/1993 | Masters | |
| 5,375,596 A | 12/1994 | Twiss et al. | |
| 5,411,503 A * | 5/1995 | Hollstien et al. | 606/86 R |
| 5,522,803 A | 6/1996 | Teissen-Simony | |
| 5,581,185 A | 12/1996 | Petropoulos et al. | |
| 5,607,407 A | 3/1997 | Tolkoff et al. | |
| 5,620,419 A | 4/1997 | Lui et al. | |
| 5,638,819 A | 6/1997 | Manwaring et al. | |
| 5,645,065 A | 7/1997 | Shapiro et al. | |
| 5,676,673 A | 10/1997 | Ferre et al. | |
| 5,758,667 A | 6/1998 | Slettenmark | |
| 5,879,297 A | 3/1999 | Haynor et al. | |
| 5,913,820 A * | 6/1999 | Bladen et al. | 600/407 |
| 5,948,006 A | 9/1999 | Mann | |
| 5,957,890 A | 9/1999 | Mann et al. | |
| 6,009,878 A | 1/2000 | Weijand et al. | |
| 6,073,043 A * | 6/2000 | Schneider | 600/424 |
| 6,129,668 A | 10/2000 | Haynor et al. | |
| 6,161,032 A * | 12/2000 | Acker | 600/424 |
| 6,235,038 B1 | 5/2001 | Hunter et al. | |
| 6,263,230 B1 | 7/2001 | Haynor et al. | |
| 6,282,437 B1 | 8/2001 | Franck et al. | |
| 6,287,293 B1 | 9/2001 | Jones et al. | |
| 6,289,250 B1 | 9/2001 | Tsuboi et al. | |
| 6,293,922 B1 | 9/2001 | Haase | |
| 6,298,262 B1 | 10/2001 | Franck et al. | |
| 6,305,381 B1 | 10/2001 | Weijand et al. | |
| 6,351,662 B1 | 2/2002 | Franck et al. | |
| 6,428,504 B1 | 8/2002 | Riaziat et al. | |
| 6,453,198 B1 * | 9/2002 | Torgerson et al. | 607/29 |
| 6,482,182 B1 | 11/2002 | Carroll et al. | |
| 6,493,573 B1 | 12/2002 | Martinelli et al. | |
| 6,516,212 B1 | 2/2003 | Bladen et al. | |
| 6,529,765 B1 | 3/2003 | Franck et al. | |
| 6,534,982 B1 * | 3/2003 | Jakab | 600/424 |
| 6,540,756 B1 | 4/2003 | Vaughan | |
| 6,546,277 B1 | 4/2003 | Franck et al. | |
| 6,547,755 B1 | 4/2003 | Lippe et al. | |
| 6,569,143 B2 * | 5/2003 | Alchas et al. | 604/506 |
| 6,636,757 B1 | 10/2003 | Jascob et al. | |
| 6,689,142 B1 | 2/2004 | Tremaglio, Jr. et al. | |
| 6,701,179 B1 | 3/2004 | Martinelli et al. | |
| 6,717,397 B2 | 4/2004 | Sorenson, Jr. | |
| 6,729,370 B2 * | 5/2004 | Norton et al. | 141/329 |
| 6,740,076 B2 | 5/2004 | Hoben et al. | |
| 6,774,624 B2 * | 8/2004 | Anderson et al. | 600/424 |
| 6,788,967 B2 * | 9/2004 | Ben-Haim et al. | 600/424 |
| 6,792,303 B2 * | 9/2004 | Taimisto | 600/424 |
| 6,805,687 B2 | 10/2004 | Dextradeur et al. | |
| 6,879,160 B2 * | 4/2005 | Jakab | 600/424 |
| 6,895,268 B1 | 5/2005 | Rahn et al. | |
| 7,044,932 B2 * | 5/2006 | Borchard et al. | 604/116 |
| 7,174,202 B2 | 2/2007 | Bladen et al. | |
| 7,313,430 B2 | 12/2007 | Urquhart et al. | |
| 7,347,843 B2 | 3/2008 | Adams et al. | |
| 7,366,562 B2 | 4/2008 | Dukesherer et al. | |
| 7,599,730 B2 | 10/2009 | Hunter et al. | |
| 7,846,164 B2 | 12/2010 | Castillo et al. | |

| | | | |
|---|---|---|---|
| 2001/0044578 A1 | 11/2001 | Ben-Haim et al. | |
| 2002/0036326 A1 | 3/2002 | DeJong et al. | |
| 2002/0193685 A1 * | 12/2002 | Mate et al. | 600/424 |
| 2003/0060763 A1 * | 3/2003 | Penfold et al. | 604/116 |
| 2003/0114752 A1 | 6/2003 | Henderson et al. | |
| 2003/0160721 A1 * | 8/2003 | Gilboa et al. | 600/424 |
| 2004/0064030 A1 | 4/2004 | Forsell | |
| 2004/0078000 A1 | 4/2004 | Borchard et al. | |
| 2004/0133101 A1 * | 7/2004 | Mate et al. | 600/426 |
| 2004/0199220 A1 | 10/2004 | Cantlon | |
| 2004/0267121 A1 | 12/2004 | Sarvazyan et al. | |
| 2005/0027304 A1 * | 2/2005 | Leloup et al. | 606/102 |
| 2005/0049486 A1 | 3/2005 | Urquhart et al. | |
| 2005/0065435 A1 | 3/2005 | Rauch et al. | |
| 2005/0085714 A1 | 4/2005 | Foley et al. | |
| 2005/0085720 A1 | 4/2005 | Jascob et al. | |
| 2005/0187515 A1 | 8/2005 | Varrichio et al. | |
| 2005/0203380 A1 | 9/2005 | Sauer et al. | |
| 2005/0249667 A1 | 11/2005 | Tuszynski et al. | |
| 2005/0256451 A1 | 11/2005 | Adams et al. | |
| 2006/0089619 A1 | 4/2006 | Ginggen | |
| 2006/0106292 A1 * | 5/2006 | Anderson | 600/301 |
| 2006/0124140 A1 | 6/2006 | Forsell | |
| 2006/0224129 A1 | 10/2006 | Beasley et al. | |
| 2006/0247584 A1 | 11/2006 | Sheetz et al. | |
| 2007/0123823 A1 | 5/2007 | Cantlon | |
| 2007/0213837 A1 | 9/2007 | Ferreri et al. | |
| 2007/0285251 A1 | 12/2007 | Kim et al. | |
| 2008/0051722 A1 | 2/2008 | Ellsmere et al. | |
| 2008/0083413 A1 | 4/2008 | Forsell | |
| 2008/0132909 A1 | 6/2008 | Jascob et al. | |
| 2008/0140025 A1 | 6/2008 | Sheetz et al. | |
| 2008/0204004 A1 | 8/2008 | Anderson | |
| 2008/0250340 A1 | 10/2008 | Dlugos et al. | |
| 2008/0281279 A1 | 11/2008 | Hoendervoogt et al. | |
| 2008/0287771 A1 * | 11/2008 | Anderson | 600/424 |
| 2008/0287776 A1 * | 11/2008 | Ephrath et al. | 600/424 |
| 2009/0039075 A1 | 2/2009 | Wang | |
| 2009/0069750 A1 * | 3/2009 | Schraga | 604/167.02 |
| 2009/0082782 A1 | 3/2009 | Kalpin | |
| 2009/0137899 A1 | 5/2009 | Bengtson | |
| 2009/0221907 A1 * | 9/2009 | Bar-Tal | 600/424 |
| 2009/0222066 A1 * | 9/2009 | Chen et al. | 607/61 |
| 2009/0227863 A1 | 9/2009 | Bzostek et al. | |
| 2009/0234302 A1 * | 9/2009 | Hoendervoogt et al. | 604/288.01 |
| 2010/0016835 A1 | 1/2010 | Davey | |
| 2010/0030150 A1 * | 2/2010 | Paques et al. | 604/116 |
| 2010/0076305 A1 | 3/2010 | Maier-Hein et al. | |
| 2010/0331782 A1 | 12/2010 | Hendriks et al. | |
| 2011/0112611 A1 * | 5/2011 | Aghassian | 607/60 |
| 2011/0237935 A1 | 9/2011 | Kalpin et al. | |
| 2011/0237937 A1 | 9/2011 | Kalpin et al. | |
| 2011/0238034 A1 | 9/2011 | Kalpin et al. | |
| 2012/0087557 A1 | 4/2012 | Miller et al. | |
| 2013/0296830 A1 | 11/2013 | Kalpin et al. | |

FOREIGN PATENT DOCUMENTS

| | | | |
|---|---|---|---|
| EP | 1832254 A1 | | 9/2007 |
| EP | 1832254 A1 * | | 9/2007 |
| EP | 1898293 A1 | | 3/2008 |
| WO | WO-9729709 A1 | | 8/1997 |
| WO | WO-2007136784 A2 | | 11/2007 |
| WO | WO-2009039075 A1 | | 3/2009 |
| WO | WO-2009039077 A1 | | 3/2009 |
| WO | WO-2011119416 A1 | | 9/2011 |
| WO | WO-2011119417 A1 | | 9/2011 |
| WO | WO-2011119418 A2 | | 9/2011 |
| WO | WO-2011126694 A1 | | 10/2011 |

OTHER PUBLICATIONS

"AxiEM Electromagetic Navigation," tri-fold brochure, Medtronic Navigation (2005) 2 pages.
"StealthStation_S7_System® Information Center in the OR," (2009) Medtronic, Inc.
"StealthStation® i7™ Integraphted Navigation System, Optimize Your Surgical Space," brochure. (2009) Medtronic Navigation, Inc.

(56) References Cited

OTHER PUBLICATIONS

Medtronic Navigation, "StealthStation® AXIEM™ Electromagnetic Navigation . . . ", 2005, www.stealthstation.com/physician/spine/library/axiem_ent.jsp, printed Aug. 19, 2006 (2 pages).
International Search Report and Written Opinion mailed Jun. 28, 2011 for PCT/US2011/028915, which claims benefit of U.S. Appl. No. 61/317,563; of which U.S. Appl. No. 13/045,684, filed Mar. 11, 2011 also claims benefit.
International Search Report and Written Opinion mailed Jul. 7, 2011 for PCT/US2011/028856, which claims benefit of U.S. Appl. No. 13/045,683, filed Mar. 11, 2011.
International Search Report and Written Opinion mailed Jun. 29, 2011 for PCT/US2011/028916, which claims benefit of U.S. Appl. No. 13/045,681, filed Mar. 11, 2011.
International Preliminary Report on Patentability mailed Oct. 4, 2012, for PCT/US2011/028916, which claims benefit of U.S. Appl. No. 13/045,681, filed Mar. 11, 2011.
International Preliminary Report on Patentability mailed Oct. 4, 2012, for PCT/US2011/028856, which claims benefit of U.S. Appl. No. 13/045,683, filed Mar. 11, 2011.
International Preliminary Report on Patentability mailed Oct. 4, 2012, for PCT/US2011/028915, which claims benefit of U.S. Appl. No. 13/045,684, filed Mar. 11, 2011.
International Preliminary Report on Patentability mailed Oct. 4, 2012, for PCT/US2011/028918, which claims benefit of U.S. Appl. No. 13/045,686, filed Mar. 11, 2011.
USPTO Office Action mailed Oct. 15, 2012 for U.S. Appl. No. 13/045,681.
USPTO Office Action (Restriction Requirement) mailed Aug. 2, 2012 for U.S. Appl. No. 13/045,681.
USPTO Office Action (Restriction Requirement) mailed Oct. 5, 2012 for U.S. Appl. No. 13/045,683.
USPTO Office Action mailed Oct. 12, 2012 for U.S. Appl. No. 13/045,684.
USPTO Office Action (Restriction Requirement) mailed Nov. 8, 2012 for U.S. Appl. No. 13/045,686.
USPTO Notice of Allowance mailed Mar. 4, 2013 for U.S. Appl. No. 13/045,681.
USPTO Notice of Allowance mailed Mar. 5, 2013 for U.S. Appl. No. 13/045,683.
USPTO Office Action mailed Mar. 4, 2013 for U.S. Appl. No. 13/045,684.
USPTO Office Action mailed Apr. 25, 2014 for U.S. Appl. No. 13/936,852.
USPTO Office Action mailed Aug. 21, 2014 for U.S. Appl. No. 13/045,686.

* cited by examiner

METHOD AND APPARATUS FOR GUIDING AN EXTERNAL NEEDLE TO AN IMPLANTABLE DEVICE

CROSS-REFERENCE TO RELATED APPLICATIONS

This application claims the benefit of U.S. Provisional Patent Application No. 61/317,563 filed on Mar. 25, 2010. The disclosure of the above application is incorporated herein by reference.

FIELD

The present disclosure relates to a system for navigating an instrument to a selected location, and more particularly to a method and apparatus for guiding an external needle to an implantable medical device.

BACKGROUND

This section provides background information related to the present disclosure which is not necessarily prior art.

Implantable or implanted medical devices are often placed sub-dermally in a body of a patient. The implanted medical device can be provided for various purposes, but include implanted infusion devices that include pumps. The pumps in the implanted medical devices infuse a material, such as a functional material or functional fluid into the patient. The pump can be programmed to infuse the functional material at a selected rate, based on a selected physiological sensing, etc. Over a period of time, however, the reservoir in the implanted medical device may empty thus requiring the reservoir to be refilled to continue operation.

Refilling an implanted medical device requires accessing the reservoir of the implanted medical device. Accessing the reservoir, however, may be difficult and require open access to the implanted device. Selected devices include ports through which a needle can be placed. The port can be found through the dermis of the patient by palpation. Also, a Hall Effect sensor can be used to determine the position of the port. Both of these methods, however, can lack the ability to determine the orientation of the refilling system relative to the implanted medical device and the precise location of the port.

SUMMARY

This section provides a general summary of the disclosure, and is not a comprehensive disclosure of its full scope or all of its features.

A navigation system can determine precise orientation and position of a delivery system relative to an implanted or implantable medical device (IMD). The IMD can include a localizer formed of one or more transmitting coils that transmit a navigation region or field. An antenna can include one or tracking devices. The tracking devices can be sensors. According to various embodiments, the sensors can include one or more coils that can sense the field generated by the localizer in the navigation region. The antenna can be associated with a support tool and/or a delivery container to determine the location of the support tool and/or a delivery container. The location of the support tool and/or a delivery container can then be displayed on a display device for viewing by a user during a refilling procedure.

According to various embodiments, a system for generating a field relative to an implanted medical device (IMD) may include a coil array positioned in the implanted medical device including a plurality of coils each having a winding group formed on a flexible circuit. The IMD can include a single power source in the implanted medical device to power all components of the implanted medical device including the coil array. A processor operable to energize the coil array according to selected instructions to assist in providing a substantially constant current to the coil array may also be provided in the IMD. Each of the plurality of coils in the coil array is formed substantially thin in the flexible circuit to provide a substantially thin profile of the flexible circuit.

According to various embodiments, a method of operating a localizer associated with an implanted medical device having a single power source to generate a navigation field and transmit telemetry from the implanted medical device is disclosed. The method can include operating the implanted medical device to deliver a therapy to a patient including drawing a current from the single power source. A stop signal can be sent to a receiver in the implanted medical device to stop the operation of the implanted medical device from delivering the therapy. In response to the stop signal, the operation of the implanted medical device can be stopped from delivering the therapy. After stopping operation of the implanted medical device from delivering the therapy, a port finder routine can be started having sub-routines including: starting a port finder timer to time the operation of the port finder routine; and powering a coil to emit a field; determining whether the port finder timer has expired. When it is determined that the port finder timer has expired, then operation of the implanted medical device to deliver the therapy can be restarted.

According to various embodiments, a system to provide a constant current to a localizer in an implanted medical device is disclosed. The system can include an operational amplifier operable to receive an input voltage and output a reference voltage to a precision resistor and a first PMOS current mirror cascode. The system can further include a NMOS current mirror operable to receive an output voltage from the precision resistor; a second PMOS current mirror cascode operable to receive an output voltage from the nmos current mirror and the first PMOS current mirror cascode to output a substantially constant current based on the output reference voltage. A first coil, a first capacitor, and a first switch can be provided to form a connection between the second PMOS current mirror cascode and the first coil and the first capacitor. The first capacitor is operable to tune the frequency of the output from the first coil to a selected frequency.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

The following description of various embodiments is merely exemplary in nature and is in no way intended to limit the teachings, its application, or uses. By way of example, the following description is directed toward a delivery system for delivering a functional fluid to an implantable device, such as an implantable infusion device. It is appreciated, however, that the following may be used for other systems without departing from the scope of the present disclosure.

I. Introduction

Figure 1:
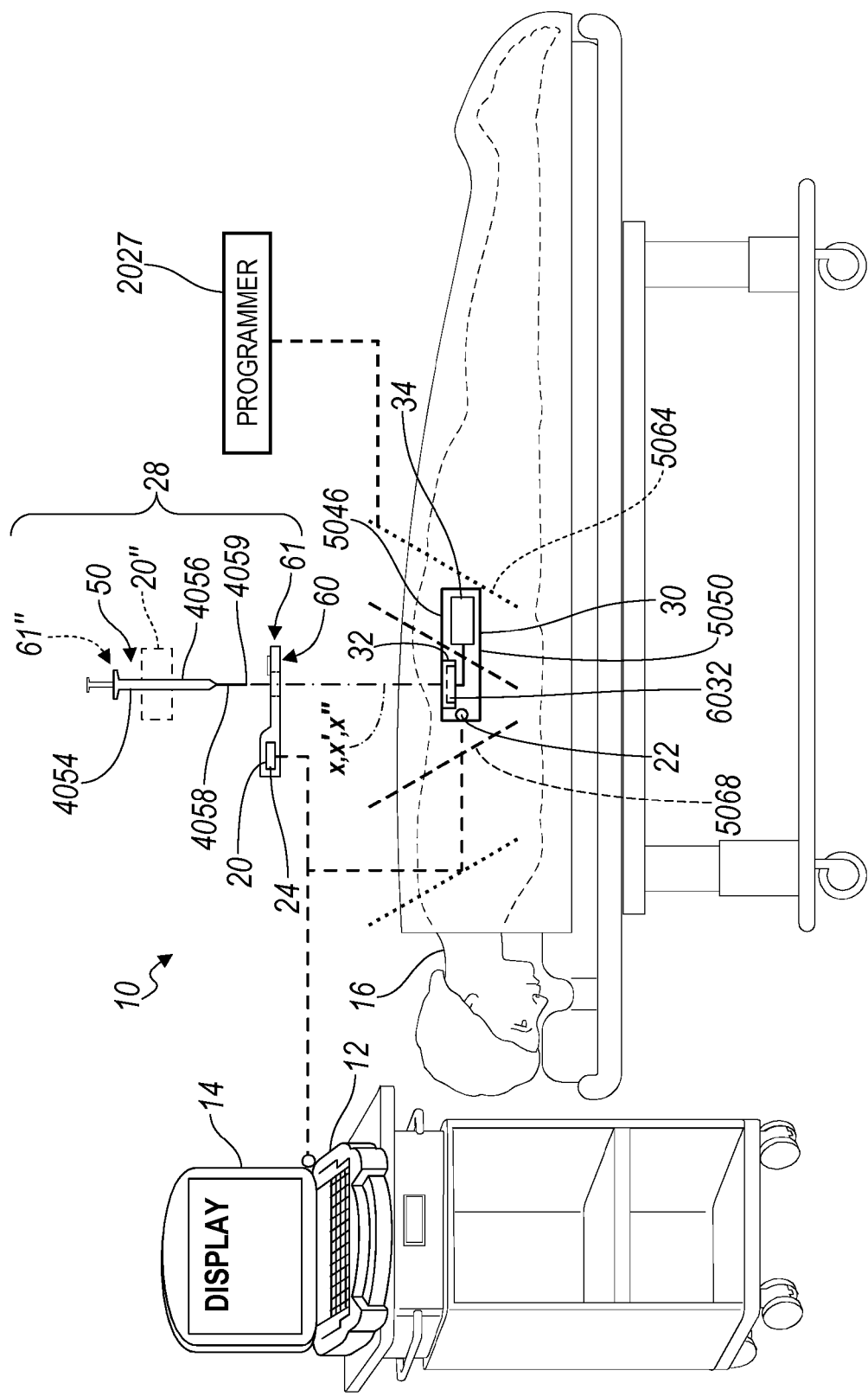
FIG. 1 is a schematic illustration of a navigation system and a delivery system according to various exemplary embodiments of the present disclosure.

FIG. 1 schematically illustrates a navigation system 10 according to various exemplary embodiments of the present disclosure. The navigation system 10 can include a processor system 12 as discussed further herein. Exemplary navigation systems include those disclosed in U.S. Pat. No. 7,366,562, issued on Apr. 29, 2008 to John H. Dukesherer et al. and U.S. Pat. App. Pub No. 2008/0132909, published Jun. 5, 2008, to Bradley A. Jascob et al., both incorporated herein by reference. Commercial navigation systems include the StealthStation® AxiEM™ Surgical Navigation System sold by Medtronic Navigation, Inc. having a place of business in Louisville, Colo., USA. Generally, the processor system 12 can be a controller that includes one or more processors (e.g. processor cores), either in a single box or a container, or in several containers.

The processor system 12 can process an image for display on a display device 14 and receive and transmit information regarding a location, where location information can include both x, y, and z position and roll, pitch, and yaw orientation information, of a tracking device 20 associated with a tracked instrument 61 (including those discussed hereinbelow) relative to a localizer 22. Accordingly, six degree of freedom (6 DOF) information can be determined with a tracking or navigation system. The localizer 22 can be used to determine a location of the tracking device 20 and, in turn, the location of the tracked instrument 61 can be determined relative to the localizer based on the tracked location of the tracking device 20. The localizer 22 can be associated with a device implanted in a patient 16, which can be referred to as an implanted or implantable medical device (IMD) 30.

In various embodiments, the tracking device 20 has an antenna or receiving coil array 24 that receives or senses information from the localizer 22. The localizer 22 can include a transmit coil array that transmits or emits a field, such as an electromagnetic field, that can be sensed by the antenna 24 of the tracking device 20. According to various embodiments, it will be understood that the antenna 24 of the tracking device 20 can also be powered to transmit a field that is received by the localizer 22. Thus, the tracking device 20 can be operated to transmit or receive a signal and the localizer 22 can operate to do the opposite of the tracking device 20.

FIG. 1 also schematically illustrates a delivery system 28. In some embodiments, the delivery system 28 can include a supply assembly 50 (including a container and a hypodermic needle or the like). The delivery system 28 can also include a support tool or guide 60. As will be discussed, the delivery system 28 can be used for delivering a functional fluid from outside the patient 16 to a the IMD 30 that is implanted within the patient 16. Also, the support tool 60 can be used for stabilizing and guiding the supply assembly 50 relative to the patient 16 during use.

The tracking device 20 can be operably coupled to the support tool 60 or alternatively to the supply assembly 50. For instance, in the embodiment of FIG. 1, the tracking device 20 can be operably coupled to the support tool 60 to allow the support tool 60 to be tracked (i.e., the support tool 60 can be the tracked instrument 61). In other embodiments, the tracking device 20" (shown in phantom) can be operably coupled to the supply assembly 50 to allow the supply assembly 50 to be tracked (i.e., the supply assembly 50 can be the tracked instrument 61"). As such, the navigation system 10 can be used to detect the location of the tracked instrument 61, 61" of the delivery system 28. This can facilitate delivery of the functional fluid from the delivery system 28 to the IMD 30, as will be discussed in greater detail below.

In some embodiments, the implantable device 30 can include a port 32 and a reservoir 34. The port 32 can define an insertion axis X, and the port 32 can be located entirely within the patient 16 (e.g., beneath the patients dermis or skin). Also, the port 32 can be in fluid communication with the reservoir 34. Functional fluid from the delivery system 28 can be delivered to the reservoir 34 via the port 32. Once delivered, the implantable device 30 can supply the patient 16 with the functional fluid on a predetermined basis or as needed basis. For instance, the IMD 30 can be an implantable infusion device, and the functional fluid within the reservoir 34 can be any appropriate fluid, such as an analgesic, insulin, insulin substitute, hormone treatment, or any other appropriate treatment. The IMD 30 can pump the functional fluid to predetermined tissue of the patient 16 according to a predetermined schedule to maintain the health, pain control, or other physiological features of the patient 16. The IMD 30 can also function to deliver the therapy based on sensed physiology of the patient 16. Exemplary embodiments of the implantable device 30 include the infusion systems SYNCHROMED® II Drug Infusion System, Models 8637-20, 8637-40, SYNCHROMED® EL Drug Infusion System, Model 8627, ISOMED® Constant Flow Infusion System, Models 8472-20, 8472-35, 8472-60 sold by Medtronic, Inc. having a place of business in Minneapolis, Minn., USA.

The IMD 30 may also include a pumping system and connections to allow for pumping of the functional material from the reservoir 34 to the patient 16 as required. Further, the IMD 30 can include a processor and memory portions with programming for delivering the functional fluid to the patient 16 at a selected time and rate and for other programmed operations. As the functional fluid is evacuated from the reservoir 34, the reservoir 34 may be refilled at selected times using the delivery system 28 and the navigation system 10.

II. Implanted Medical Device Coil Array/Localizer

Figure 2:
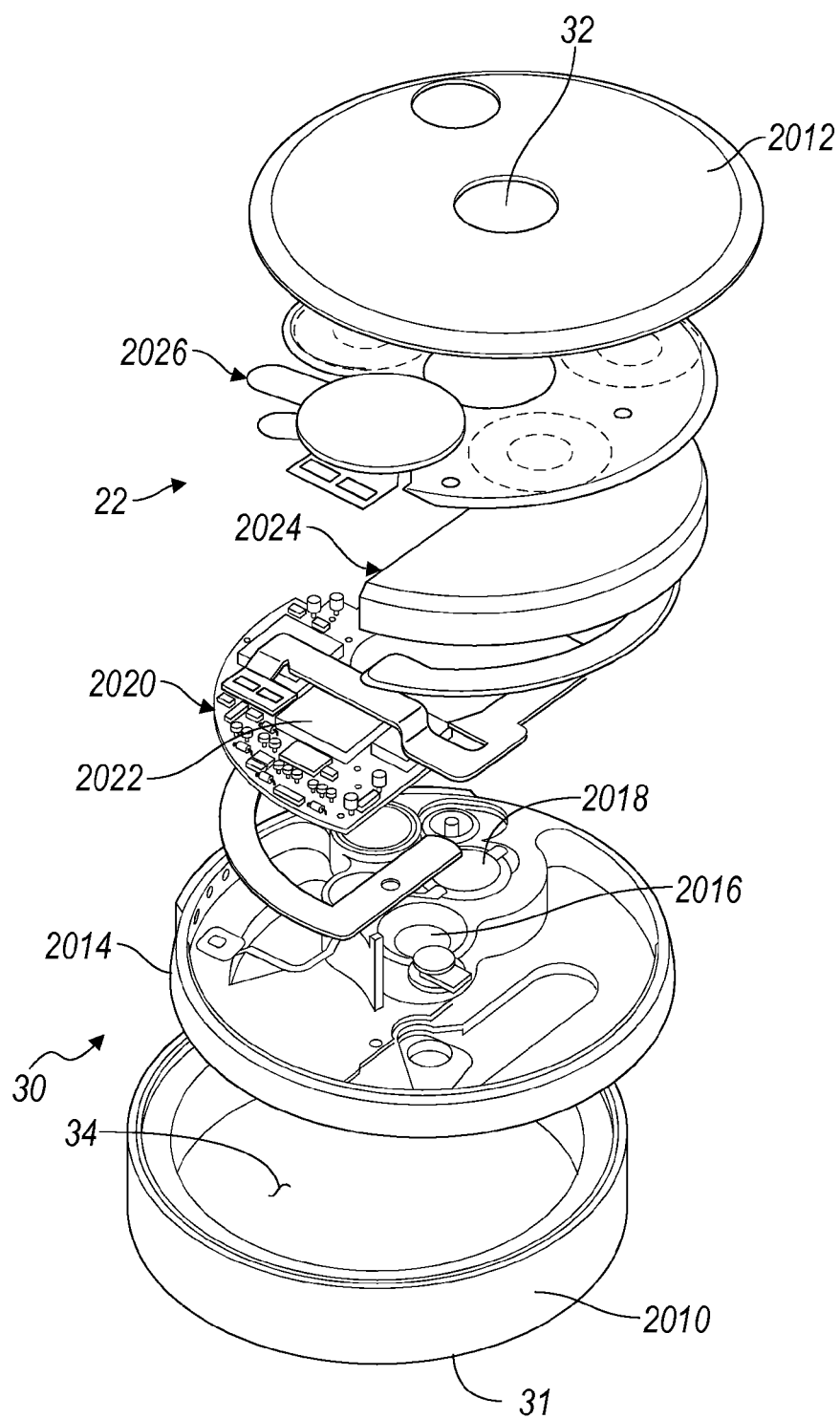
FIG. 2 is an exploded perspective view of an implanted medical device.

With reference to FIG. 1, and additional reference to FIG. 2, the IMD 30 can include several portions assembled within a casing 2010 that can be closed with a top lid or top casing 2012. The top casing 2012 can define the port 32 through which the delivery system 28 can be used to fill the reservoir 34. The reservoir 34 is defined within the casing 2010 and can be filled with the appropriate functional fluid. The reservoir 34 can be closed with a top cap or top portion 2014. A septum or internal port 2016 can be defined by the internal cap 2014.

The implanted medical device 30 can house various components that are necessary or selected for operation of the implanted medical device 30. For example, a pump 2018 can be positioned on the top plate 2014. Interconnected or positioned relative to the top plate 2014 can also be a first printed circuit board (PCB) 2020. The printed circuit board can include various circuitry, including an internal or implanted medical device processor 2022. It will be understood that other circuitry can also be included with the internal (PCB) 2020, but the processor 2022 can be used to execute selected instructions that can be stored in a memory that is also on the internal (PCB) 2020 and/or can also be included with the processor 2022. The processor 2022 can be one or more appropriate processors that are selected and used in various implanted medical devices such as the implanted medical device infusion systems disclosed above and, sold by Medtronic, Inc., having a place of business in Minneapolis, Minn.

Also included within the implanted medical device 30 can be a power source, such as a battery 2024 that is used to power the various components of the implanted medical device 30, including the pump 2018 and the processor 2022. The battery 2024 can also be used to power the transmitter coil array (as discussed herein) of the localizer 22 that is printed or etched onto a second printed circuit board 2026. The second PCB 2026 can also be referred to as the localizer or coil array PCB 2026, herein. The power source can include only one or a plurality of batteries or other chargeable and power storage systems (e.g. capacitors). Including a single battery, however, can allow a more efficient power and component design.

The top casing 2012 can be sealed to the body casing 2010 to enclose all of the components of the IMD 30 prior to implantation in the patient 16. As is understood by one skilled in the art, the coil array PCB 2026 can be used to transmit or receive data as a part of a telemetry system to either program or receive data from the internal processor 2022, store information in an internal memory system or retrieve information from an internal memory system, or any other appropriate task relative to the IMD 30. It will also be understood that the IMD 30 may also include an additional antenna in addition to the coil array PCB 2026 for telemetry purposes. Additional antennas, such as a telemetry antenna can be formed on an exterior of the case top 2012. The telemetry system can be used to communicate with the processor 12 of the navigation system 10 or with a separate programmer 2027 that can be used to program the delivery of the functional material from the IMD 30 or sensed physiological events.

According to various embodiments, however, the single battery 2024 can be used to power all of the components and portions of the IMD 30. The single battery or other power supply can power the pump 2018, the processor 2022, the localizer 22, and other various components that may require power during the life cycle of the 30. Accordingly, it can be selected to provide a power conserving system, as discussed herein.

Figure 3:
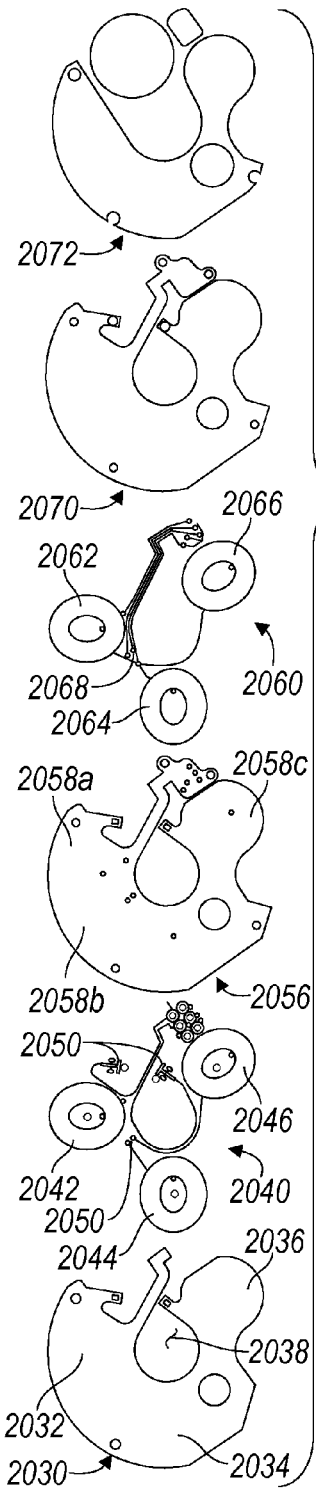
FIG. 3 is an exploded schematic of a transmitter coil array.

With a continued reference to FIG. 2 and additional reference to FIG. 3, the coil array PCB 2026 is illustrated. The coil array PCB 2026 can be formed by layering a plurality of portions to form a PCB or flex circuit 2026. The coil array PCB 2026, as illustrated in the exploded view in FIG. 3, can include a far side or bottom layer 2030. The bottom layer or far side 2030 can be the layer that is positioned closest to the internal top plate 2014 in the implanted medical device 30. The bottom layer 2030 can be formed of appropriate materials, such as polyimide. The bottom layer 2030 can include coil array areas 2032, 2034 and 2036, onto which the coil arrays, or at least a portion of the coil arrays, can be positioned, as discussed further herein. The coil array areas 2032-2036, are open areas that can be filled with the coil array material. The bottom layer 2030 can also include an opening or a passage 2038 that extends from the external port 32 to the internal port 2016. Accordingly, the passage 2038 substantially defines the target or area through which a piercing member 4058 may pass to fill the reservoir 34 of the implanted medical device.

A first portion or first layer of the coil array 2040 can be formed directly on the bottom layer in the coil array areas 2032-2036. The first coil array portion 2040 can include three coils or coil parts including a first coil 2042, a second coil 2044, and a third coil 2046. These coils 2042-2046 can be respectively positioned on the bottom layer 2030 in the respective positions 2032, 2034, and 2036. The coils 2042-2046 can be formed by appropriate mechanisms including copper deposition methods onto the bottom layer 2030. It will be understood that the coils 2042-2046 can be formed by other mechanisms including etching, thin wire coiling, deposition (including vacuum, vapor, sputtering), and other appropriate mechanisms or techniques. The coils 2042-2046 can be formed as continuous lengths or spirals of conductive material, such as the copper, on the bottom layer 2030. The coils 2042-2046 can be formed to include a selected number of turns to achieve an appropriate field strength when powered or a current is driven through the coils 2042-2046. The field strength can be selected by the current per conductive path, the number of conductive paths, and the geometry of the conductive paths. For example where the geometries are convex, the area enclosed by the conductive paths can select the field strength. Thus, the field strength can be augmented by selection of turns and the number of coil portions, as discussed below.

In addition, the width of the coils or traces of the coil can be selected to achieve the selected number of turns. The number of turns in the coils 2042-2046 can include about 10 turns to about 100 turns, including about 35 turns to about 45 turns, and further including about 38 turns to about 42 turns. The number of turns can be selected to achieve a proper density of coil turns in the coil array or select a field strength, including about 38 turns to 42 turns of a trace or wire having a selected thickness. The thickness of the traces or wire can be selected to be about 0.001 inches (in.) (about 0.025 millimeters (mm)) to about 0.01 in. (about 0.25 mm) including about 0.0019 in. (about 0.0483 mm) to about 0.008 in. (about 0.203 mm). The two ends of each of the coils 2042-2046 can terminate in terminal portions 2050. The terminal portions can be positioned near vias or passages in an insulation or isolation layer 2056. The isolation layer 2056 can be an appropriate material, such as a polyimide that can isolate the first coil portion 2040 from a second coil portion 2060. The isolation layer 2056 insulates or isolates the coils 2042-2046 of the first coil array portion 2040 from the second coil array portion 2060 including the coil parts 2062, 2064, and 2066. Thus, the first coil array portion 2040 does not short to the second coil array portion 2060.

The second coil array portion 2060 can also include three coils or coil parts 2062, 2064, and 2066 formed as lengths of material generally forming spirals. The coils 2062-2066 of the second coil array portion 2060 can be positioned over or relative to the isolation layer 2056 in coil areas 2058a, 2058b, and 2058c. The coils 2062-2066 can be formed on the isolation layer 2056 in a manner substantially similar to forming the first coil array portion 2040 on the bottom layer 2030. Accordingly, the coils 2062-2066 of the second coil array portion 2060 can be formed by copper deposition, etching, thin wire coiling, or the like. Additionally, the number of turns in the coils 2062-2066 or the second coil array portion 2060 can also be selected to be the same, a larger number, or smaller number, than the coils in the first coil array portion 2040. Generally, the coils are selected to include an identical number of turns in the coils 2042-2046 of the first coil array portion 2040 to the respective coils 2062-2066 in the second coil array portion 2060. The second coil array portion 2016 generally overlays and is substantially identical to the coils in the first coil array portion 2040 with the isolation layer 2056 separating the two.

Vias through the isolation layer 2056 allow connection of the terminal portions 2050 of each of the first coils 2042-2046 of the first coil array portion 2040 to connect with terminal portions 2068 of each of the coil parts of the second coil array portion 2060 such that the first coil 2042 of the first coil array portion 2040 is in series and will act substantially as a single coil with the first coil portion 2062 of the second coil array portion 2060. Likewise for the other respective coil parts 2044 and 2064 and coil parts 2046 and 2066 form second and third coils of the localizer 22. Each of the coils 2042-2046 of the first coil array portion 2040 are in series with a single one of the respective coils 2062-2066 of the second coil array portion 2060 such that each of the coil part pairs act as a single coil. Accordingly, the localizer 22 can be formed of the two coil array portions 2040, 2060, but can substantially include three coils including a first coil formed by the combination of the coil parts 2042 and 2046, a second coil formed of the combination of the coil portions 2044 and 2064, and a third coil formed of the combination of the coil portions 2046 and 2066. It will be understood, additional coil array portions can be formed by including more coils that are separated with additional isolation layers to allow the three, four, or more coil array portions. Furthermore, only one coil array portion can be selected.

As discussed further herein, the first coil array portion 2040 and the second coil array portion 2060 can be powered by the battery 2024 to transmit or form the navigation field, including an electromagnetic field, relative to the IMD 30. The three coils of the localizer 22, discussed herein can be defined by the coil part pairs described above. Including the localizer 22 in the IMD 30 allows for a compact and contained navigation system 10 that may not require an external localizer to track the tracking device 20 and the IMD 30 to navigate the supply system 28 relative to the IMD 30.

The coil array PCB 2026 can further include a top layer 2070 and a stiffener portion 2072. All of the portions, including the bottom layer 2030, the first coil array portion 2040, the isolation layer 2056, the second coil array portion 2060, the top layer 2070, and the stiffener 2072 can be formed together as a single flex circuit or the coil array PCB 2026. The single flex circuit of the PCB 2026 can be positioned within the IMD 30. The single PCB 2026 can be formed to have a thickness from the outside of the bottom layer 2030 to the outside of the top layer 2072 to be about 0.01 in. to about 0.03 in., including about 0.0128 in. (about 0.325 millimeters (mm)) to about 0.0249 in. (about 0.63246 mm). This thickness allows the PCB 2026 to be contained within the IMD 30 without increasing or substantially increasing the size of generally available IMDs 30. Thus, the IMD 30 can be comfortably positioned in the patient 16 while providing the navigation localizer 22 in the IMD 30.

Figure 4:
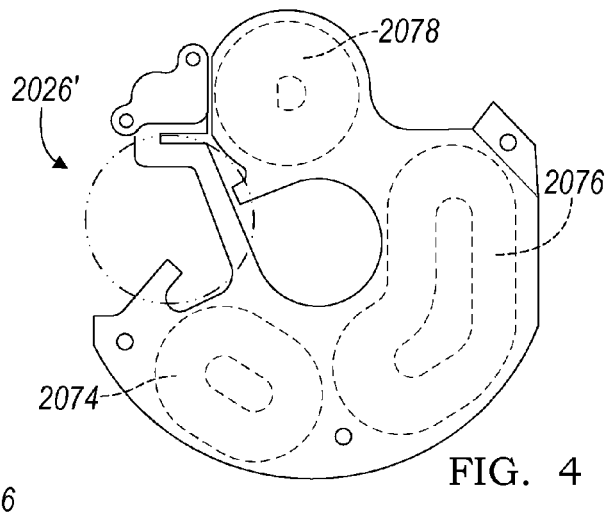
FIG. 4 is an assembled view of a transmitter coil array with various shaped coils.

As illustrated in FIG. 3, it will be understood that the coils of the coil array portions 2040, 2060 can be formed to be substantially annular or ovoid (generally oval) in exterior dimension or shape. As discussed above, the traces of the coils can be a spiral on coil array PCB 2026. It will be understood that it can be selected to form the tracings or conductive portions of the coils to be substantially thin to form a substantially thin construction, including the dimensions discussed above. Nevertheless, the shape of the coils can also be formed in selected shapes. For example, as illustrated in FIG. 4, a coil array PCB 2026 can include substantially elliptical coils 2074, "lima bean shaped" coils 2076, or circular coils or cylindrical coils 2078. By providing the coils in different shapes, substantially all the area of the coil array PCB 2026' can be covered with tracings that define coils of the localizer 22. However, including the coils to be substantially cylindrical or ovoid, can allow for the formation of a substantially uniform field with a minimum resistance in the coil tracings to achieve the appropriate field. As discussed further herein, the coil arrays of the localizer 22 formed on the coil array PCB 2026 can be used to generate the field that is sensed or received by the antenna 24 to determine a position of the delivery system 28 relative to the implanted medical device 30.

Figure 5:
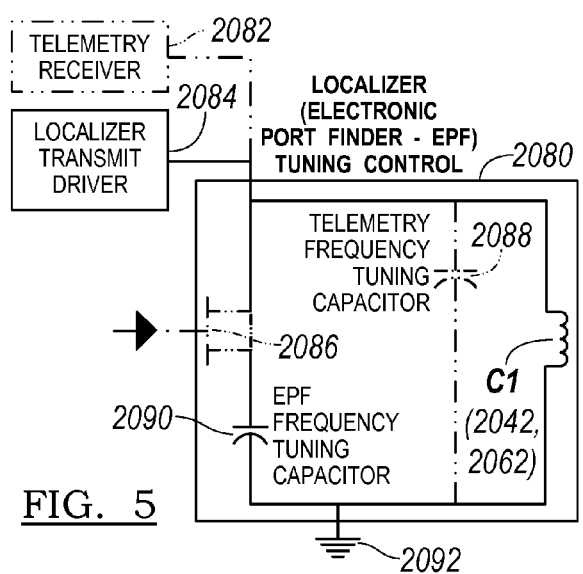
FIG. 5 is a schematic of a tuning control circuit.

With reference to FIG. 5, a tuning circuit 2080 can be included on the coil array PCB 2026 or the first internal PCB 2020 that can be used to control power consumption or tuning of the various components of the IMD 30. For example, the coil array of the localizer 22 can be powered at selected times to emit or generate the navigation field relative to the IMD 30. Alternatively, or in addition thereto, other portions can be powered to transmit telemetry data from the IMD 30. For example, a telemetry antenna 2081 can transmit a signal from the IMD 30 and can be formed in the implanted medical device 30, such as integrated in the exterior of the case 2010 or the top case 2012.

The telemetry system of the IMD 30 can operate at a selected frequency, such as about 125 (kHz). The frequency of the telemetry system can be used to transmit data regarding the IMD 30 to the processor 12 or other systems for programming the IMD 30. The coil arrays for the localizer 22, however, can be operated at other selected frequencies. For example, the coil arrays of the localizer 22 can be operated at about 40 to 50 kHz, including about 45 kHz; and further including about 10 kHz to about 50 kHz, including about 25 kHz. Accordingly, the frequency of the signal transmitted from the telemetry system may generally not interfere with the signal transmitted from the localizer 22. Nevertheless, it may be selected to transmit a signal to the telemetry system using the coils of the localizer 22 formed on the coil array PCB 2026. For example, transmitting a signal using the coils on the coil array PCB 2026 can be a back-up or in addition to transmitting telemetry without other antennas formed on the IMD 30. The use of the localizer 22 as a telemetry antenna can be done with time multiplexing techniques and the tuning circuitry 2080.

Accordingly, the tuning circuit 2080 can be provided with the IMD 30, for example on the coil array PCB 2026 or the internal PCB 2020. The tuning circuit 2080 can tune a driving signal to any one of the selected coils (e.g. formed of the coil parts). As discussed herein, a first coil C1 can exemplary include the coil formed of the coil parts 2042, 2062 in the tuning circuit 2080. It will be understood that the coil C1 can be any of the coils formed in the coil array of the localizer 22 and the coil C1 is merely exemplary. The signal driven into the tuning circuitry 2080 can be from a telemetry receiver 2082 or a localizer transmit driver 2084. The two drivers 2082, 2084 can be positioned within the IMD 30, such as on the first printed circuit board 2020.

The localizer transmit driver 2084 can be used to find the port 32 of the IMD 30, therefore it can also be referred to as an electronic port finder (EPF) or port finder (PF). Accordingly, it will be understood that discussion herein of PF can be limited to the discussion of the navigation system 10 for finding or navigating the delivery system 28 to the port 32 of the IMD 30. Accordingly, the localizer driver 2084 can also be referred to as the PF transmit driver 2084.

The tuning circuit 2080 can include a tuning control or switch 2086 to switch the incoming current to oscillate through both a telemetry frequency tuning capacitor 2088 and an EPF frequency tuning capacitor 2090 or just the telemetry tuning capacitor 2088 and the coil C1. In other words, when the switch 2086 is active the tuning circuit 2080 will be an LC circuit including the EPF tuning capacitor 2090, the telemetry tuning capacitor 2088, and the coil C1. When the switch 2086 is inactive, the tuning circuit 2080 can be a LC circuit of only the telemetry tuning capacitor 2088 and the coil C1. The circuitry can also be grounded to ground 2092 such as to an exterior of the case 2010.

When the switch 2086 is active, the circuit 2080 can generate the appropriate frequency for the EPF. When the switch 2086 is inactive the tuning circuit 2080 can generate a frequency for the telemetry system. The switch can be activated depending upon the time and which of the telemetry receiver 2082 or the localizer transmit driver 2084 is being used. The signal, from the respective drivers 2082, 2084, can be tuned to the appropriate frequency for the telemetry or the EPF system of the localizer 22 depending upon the selected feature or signal to be transmitted from the IMD 30 by the coil C1 of the localizer 22.

It can be selected, however, to achieve or attempt to achieve a maximum current through the coil C1 (or any appropriate coil). Accordingly, components in the tuning circuit 2080, according to various embodiments including those discussed herein, can be selected or varied (e.g. a capacitance of a capacitor or an inductance of the coil C1) to achieve a selected current through the coil C1. A maximum current through the EPF coils can generate a maximum field for the navigation or guiding of the supply assembly 50 relative to the IMD 30.

As exemplary illustrated in FIG. 5, when the tuning circuit 2080 is tuned to the telemetry frequency, the telemetry frequency tuning capacitor 2088 can be charged to power the coil C1 to transmit a signal from the coil C1 at the telemetry frequency. Alternatively, if the EPF is selected to be used, the switch 2086 can charge the EPF frequency tuning capacitor 2090 and the telemetry frequency tuning capacitor 2088 to power the coil C1 at the frequency for the navigation system 10. Accordingly, the tuning circuit 2080 can be used to selectively tune the coils of the localizer 22 to an appropriate frequency for either the telemetry or the EPF systems in a time multiplexing manner. As discussed above, the EPF can include navigating the delivery system 28 with the navigation system 10. It is understood, however, as illustrated in phantom in FIG. 5, the switch 2086, the telemetry tuning capacitor 2088, and the telemetry receiver 2082 need not be provided in the same tuning circuit with the EPF coils, as discussed further herein.

The tuning circuitry 2080 can be provided for each of the coils of the localizer 22. The coils can include the coil C1 mentioned above, a second coil C2 formed of the coil parts 2044, 2064, and a third coil C3 formed of the coil parts 2046, 2066. Accordingly, all of the coils of the localizer 22 can be tuned to transmit the signal at the selected frequency.

It will be understood that if a single one of the tuning circuit 2080 is used to drive each of the coils of the localizer 22, one or more switches can be provided between the tuning circuit 2080 and each of the coils. The switches (not illustrated) can individually and selectively allow driving each of the coils of the localizer 22 at the selected tuned frequency individually and alternatively at a selected time. Accordingly, it can be selected to provide switches as opposed to a plurality of the tuning circuits. As discussed herein, each of the coils can be placed in parallel with the tuning capacitors to drive each of the coils separately at the selected frequency.

Figure 5A:
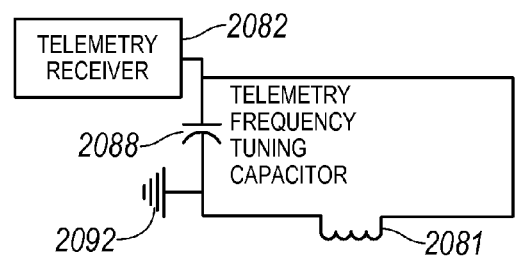
FIG. 5A is a schematic of a tuning control circuit.

It will be further understood, that additional and/or separate coils, such as the telemetry antenna 2081, illustrated in FIG. 5A, can be provided for the telemetry system that are separated from the EPF system and EPF coils C1, C2, and C3. As illustrated in FIG. 5A, a separate tuning circuit including the tuning capacitor 2088, which may include a different capacitance than when in parallel with the EPF tuning capacitor 2090, can be used when driving the telemetry antenna 2081. Also, the telemetry antenna 2081, the telemetry tuning capacitor 2088, and related connections can be placed in any appropriate location, such as the PCB 2020, of the IMD 30. Thus, providing a single tuning circuit and including one or more capacitors and switches for both the EPF system and the telemetry is not required. The coils C1, C2, and C3 (including the coil parts 2042, 2044, 2046, 2062, 2064, and 2066) therefore can be selected to be used with only the EPF system.

In an example where the tuning circuit 2080 includes only the EPF coils (as illustrated in solid lines in FIG. 5), a capacitor can be selected that does not achieve an ideal circuit resonance frequency, but can be selected for achieving a selected current through the coil or a maximum current through the coil C1 based on the input voltage. Generally, the tuning circuit 2080 can include the tuning capacitor 2090 and the coil C1 that is an inductor. A Q-factor can be determined for the tuning circuit 2080 and can be used in determining components to maximize current through the coils C1. While the inductance of the coil C1 may be selectively fixed, the capacitance can be altered to achieve a selected current though the coil C1.

As discussed above, the EPF frequency can include about 25 kHz. Using coil inductance and the target tuning frequency of about 25 kHz the resultant capacitance for resonance is about 2.2 micro-Farads (uF). The calculated resonant frequency, however, may not maximize current through the EPF coils. A high current through the coil C1, it was discovered, is achieved by tuning the circuit to a higher resonant frequency, such as to about 30 kHz to about 50 kHz, including about 40 kHz, with a 1.0 uF capacitor. It was discovered that the 1.0 uF capacitor actually increases a current through the EPF coils at the 25 Khz operational frequency relative to the tuned circuit with a 2.2 uF capacitor.

In an implanted application, capacitor aging may theoretically decrease the capacitance value of a capacitor by about 15% over 8 years of use. Thus, current changes in the EPF coils over a selected 8 year time span may change about 1% to about 3% when using a 1.0 uF capacitor and about 10% to about 20% when using a 2.2 uF capacitor. The tuning circuit 2080 including the 1.0 uF capacitor includes a reduced current variation through the coils C1 due to capacitor aging relative to the 2.2 uF capacitor. A higher resonant frequency capacitor, relative to operating frequencies, was discovered to increase current through the EPF coils (to maximize field strength with the EPF coils). Also, high resonant frequency capacitors can decrease current variance over a selected lifespan of the capacitor in the tuning circuit 2080, including a change of less than about 3%, including less than about 2%.

Again, it is understood that such a tuning circuit can include only a single capacitor or capacitor system with no switch and used to only tune the EPF coils. Further, maintaining a selected current through the coils assists in tracking or navigating the instrument with the EPF coil system by assisting in maintaining a constant or high field strength over the life span of the system. It will be understood, however, that similar principles may be applied to an antenna system for the telemetry as well.

Figure 6:
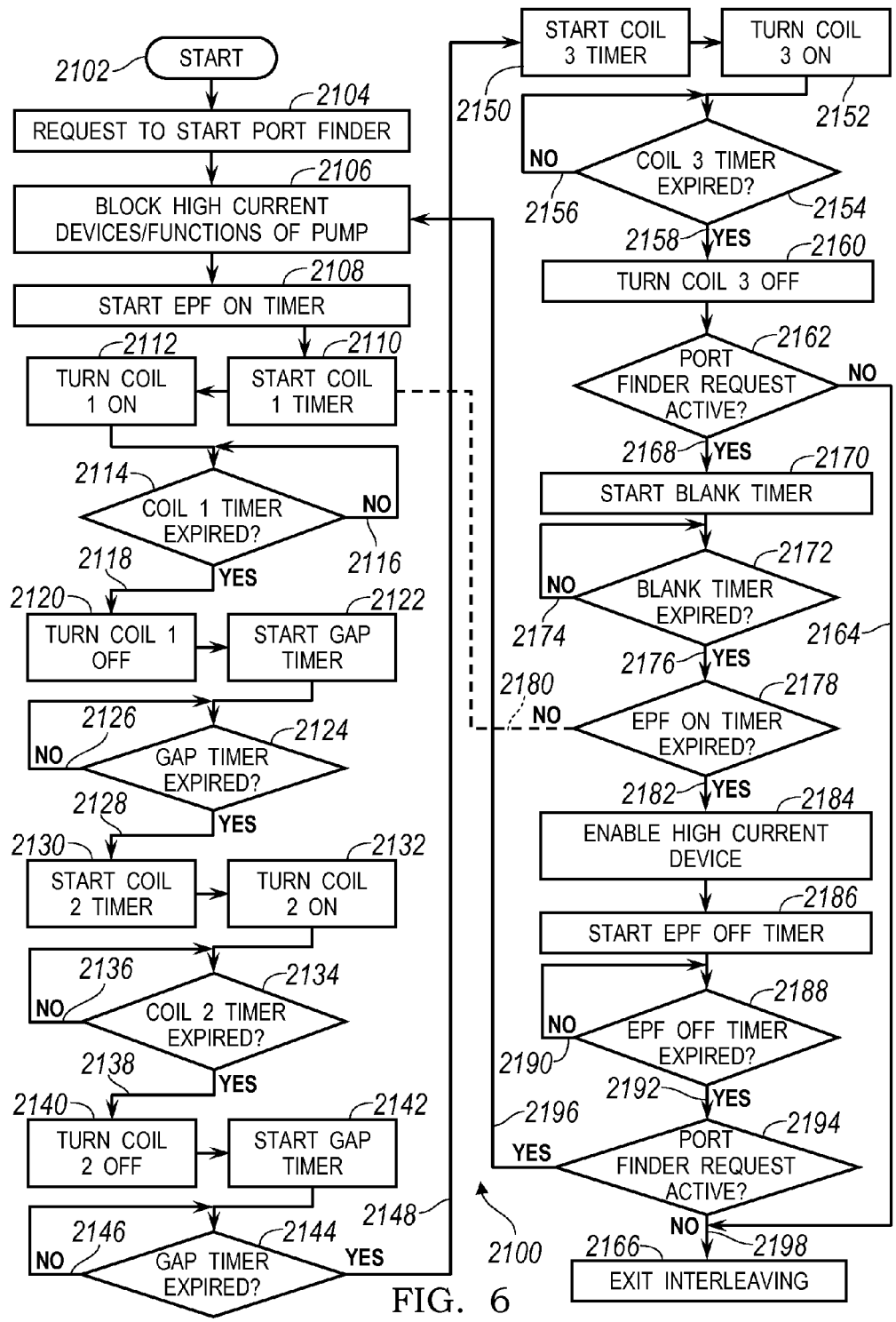
FIG. 6 is a flowchart of a power management protocol.

In reference to FIG. 6, the IMD 30 includes a battery 2024 that can power all of the components of the IMD 30. However, it can be selected to power portions of the IMD 30 separately or substantially sequentially to achieve selected results. For example, having the battery power multiple components substantially simultaneously can form or allow voltage variations and/or current variations that can be unselected or result in noisy transmissions. Accordingly, providing a power management scheme, as illustrated in a flowchart 2100, can allow for sequential powering or interleaving of powering of components of the IMD 30 to achieve all of power savings, power management, and reduced noise or constant amplitude alternating current and/or voltage from the battery 2024. The power management scheme can be implemented as instructions that are executed by a processor in the IMD 30, including the processor 2022, or can be executed and sent to the IMD 30 with the telemetry of either the navigation processor 12 or the programmer 2027.

With reference to flowchart 2100, it can start in start block 2102 which can lead to a request to start port finder in block 2104. The request to start the port finder block 2104 can come from the processor 12 or any appropriate portion of the navigation system 10. For example, the delivery system 28 can transmit a signal through the antenna 24 to the telemetry system of the IMD 30 to instigate or to request the start port finder in block 2104. Alternatively, the telemetry system, which can be provided with a programmer, can be used to send the request start port finder signal in block 2104. A signal transmitted from a system that is separate from the navigation system 10 can also send a signal to the navigation system 10 to begin receiving at the antenna 24 the signal from the localizer 22 within the implanted medical device 30. Accordingly, the request start port finder block 2104 can send a signal to the implanted medical device 30 to begin the electronic port finder power management diagram 2100 and also to the navigation system 10 to begin receiving and analyzing a signal for navigating and determining a location of the port 32 of the implanted medical device 30.

After the request start port finder is received by the IMD 30, a signal to block high current devices and other features of the IMD, such as turning off the pump 2018, can be done in block 2106 as discussed above, the IMD 30 can include a processor 2022 that, upon receiving the request port finder signal block 2104, can perform the remainder of the blocks of the algorithm illustrated in the flow charts 2100. That is, the flow chart 2100 can include steps of an algorithm that are executed by the processor 2022 to achieve the interleaving and power management in the flow chart 2100. The instructions for the algorithm can be stored on the memory included with the processor 2022 or another memory on the circuit boards, including the first circuit board 2020 or the coil array PCB 2026.

Once the high current devices, or other devices other than the powering of the localizer 22, are turned off the EPF on timer can be started in block 2108. The length of the EPF on-timer can be any appropriate amount of time, such as one to thirty seconds, or as long as selected to achieve appropriate navigation of the delivery device 28 to the port 32. The EPF on-timer can determine that the number of iterations of powering the coils of the localizer, as illustrated, in the flow chart 2100 will be cycled through to achieve port finding with the delivery system 28. In addition, it will be understood that a second or other additional request to start the port finder can be sent to the IMD 30 after the EPF on-timer has run for at least one cycle.

A coil one-timer can be started in block 2110. The coil timer can be set for a selected amount of time, such as about 100 milliseconds, including about 50 to about 200 milliseconds. Once the coil one-timer is started in block 2110, coil 1 can be turned on in block 2112. As discussed above, coil 1 as illustrated in the flow chart 2100 can include the coil parts 2042 and 2062. The flow chart 2100 will also reference coil 2 and coil 3 which can respectively include the coil parts 2044, 2064 and the coil parts 2046, 2066. Accordingly, coils 1, 2, and 3 referenced in the flow chart 2100 refer to the coil trace pairs discussed in relation to FIG. 3.

In turning on coil 1, coil 1 can be powered at the selected tuned frequency, as discussed in relation to FIG. 5. Coil 1 can be powered to emit a signal or field for navigating the delivery system 28 relative to the IMD 30. When powering the coil 1, the coil 1 can generate an electromagnetic field that can be sensed with the antenna 24 of the delivery system 28. As discussed further herein, this can allow navigation of the delivery system 28 relative to the IMD 30 to find the port 32 with a hypodermic needle 4058. In navigating, the antenna 24 of the tracking device can operate similar to tracking devices as disclosed in U.S. Patents and Patent Application Publications incorporated by reference above. By navigating the delivery system 28 to the IMD 30 a location, as discussed above, can be determined of the delivery system 28 relative to the IMD 30 to identify when the hypodermic needle 4058 is at an appropriate location for piercing the port 32. As discussed further herein, the display 14 of the navigation system 10 can be used to illustrate the delivery system 28 relative to the implanted medical device 30 including the port 32. Accordingly, the coil 1, and the other coils 2 and 3 sequentially or simultaneously can generate the field for navigating to the delivery system 28.

Once the coil 1 is powered in block 2112, a decision block 2114 of whether the coil 1 timer has expired can be made. If the decision is no, then a no path 2116 can be followed to continue powering the coil 1 in block 2112. If the timer has expired, a yes path 2118 can be followed to turn off coil 1 in block 2120. Once coil 1 is turned off, a gap timer can be started in block 2122.

The gap timer 2122 can be selected to be an appropriate time. The appropriate time can be selected to assist in distinguishing between the various coils of the localizer 22. The gap between powering coils determined by the gap timer can be about 10 to 100 milliseconds including about 50 milliseconds. Accordingly, a distinguishing gap between receiving the fields from the respective coils, including coil 1, 2, and 3, and can be used to help identify the position of the coils, the position of the port 32, and which coil or if an alternative coil is being received. Once the gap timer is started in block 2122, a decision block of whether the gap timer has expired in 2124 can be accessed. If the gap timer has not expired then a no path 2126 can be followed to continue the gap timer. Alternatively, if the gap timer has expired, then a yes path 2128 can be followed to start the coil 2 timer in block 2130.

Once the coil 2 timer has started in block 2130 coil 2 can be turned on in block 2132. As discussed above, the coil timer in block 2130 can be an appropriate length that is selected for the system and can include the same time length for the coil 1 timer. In operating coil 2, steps that are substantially similar to those for operating coil 1 are followed and will be discussed briefly here. Following coil 2, coil 3 is also operated and those steps can also be substantially similar to steps for coils 1 and 2 and will be discussed only briefly following here.

Once coil 2 is turned on then a decision block 2134 can be used to determine whether the coil 2 timer has expired. If the coil 2 timer has not expired a no path 2136 can be followed to continue powering coil 2. Alternatively, if the coil timer has expired then a yes path 2138 can be followed to turn off coil 2 and block 2140. Again, once the coil 2 is turned off then a gap timer can be started in block 2142.

Once the gap timer has been started a decision block 2144 can be used to determine whether the gap timer has expired. If the gap timer has not expired then a no path 2146 can be followed to continue the gap timer. Alternatively, if the gap timer has expired then a yes path 2148 can be followed to start the coil 3 timer in block 2150. Once the coil 3 timer has started, the coil 3 can be turned on in block 2152. Following powering the coil 3 in block 2152 a decision block 2154 of whether the coil 3 timer has expired can be used. If the coil 3 timer has not expired a no path 2156 can be followed to continue powering coil 3. Alternatively, if the coil 3 timer has expired then a yes path 2158 can be followed to turn off coil 3 in block 2160.

Once coil 3 has been turned off in block 2160 all three of the coils of the localizer 22 have been powered in sequence or in a time multiplex or division manner. Circuitry for powering the coils will be discussed in detail herein and can be used to substantially sequentially power the coils at substantially identical frequencies. Such time multiplexing can be used to transmit three different fields from the three different coils from the IMD 30. It will be understood, however, that different frequencies for each of the three coils can also be used to allow substantially powering them simultaneously. Powering the three coils of the localizer 22 simultaneously, however, can require greater power consumption from the battery 2024 and may not be selected. However, it will be understood that frequency multiplexing, allowing all of the three coils to be powered substantially simultaneously at the localizer 22 can be used.

Once the third coil is turned off in block 2160, however, the decision block of whether the port finder request is still active can be accessed in block 2162. If the port finder request is no longer active then a no path 2164 can be followed to exit the interleaving or EPF power management in block 2166. In exiting the power management in block 2166 other high current devices or other portions of the IMD 30 can be repowered. Additionally, it will be understood that an additional or further requests can be made even if the current EPF request, determined by the EPF timer is no longer active.

If the decision block of the port finder request in block 2162 is still active, then a yes path 2168 can be followed to start a blank timer in block 2170. The blank timer can be selected to be an appropriate length, which can be about 50 to 150 milliseconds, including about 100 milliseconds. The blank timer 2170 can be at a different length than the gap timer between each of the coils to assist in identifying when the third coil has been powered and when the first coil will be powered next. Accordingly, the length that the gap timer in block 2170 can be used to assist in identifying when a complete cycle of powering all three coils has been completed. The length of the gap timer in block 2170, therefore, can be programmed and saved with the navigation system 10 to assist in determining when all three coils have been powered.

Once the blank timer has been started in block 2170, a decision block of whether the blank timer has expired in block 2172 can be accessed. If the blank timer has not expired, a no path 2174 can be followed to continue the blank timer block 2170. Alternatively, if the blank timer has expired, then a yes path 2176 can be followed to a decision block of whether the EPF on-timer has expired in block 2178. If the decision that the EPF on-timer has not expired then a no path 2180 can be followed to start the coil 1 timer again in block 2110. If the decision is that the EPF on-timer has expired then a yes path 2182 can be followed to enable the high current devices in block 2184 that were blocked or turned off in block 2106. These can include powering the pump 2018, the telemetry system, or other system of the implanted medical device 30.

After the high current devices are enabled in block 2184 an EPF off-timer can be started in block 2186. Once the EPF off-timer is started, a decision block 2188 can determine whether the EPF off-timer has expired. If the EPF timer has not expired in block 2188 then a no path 2190 can be followed to continue the EPF off-timer and block 2186. However, if it is determined that the EPF off-timer has expired, then a yes path 2192 can be followed to a new decision block of whether a port finder request is still active in block 2194.

As discussed above, additional EPF active requests can be made even after a first EPF request has been made. Accordingly, a second request can be made after the EPF off-timer has been turned on in block 2186. If an additional request has been made in the decision block in 2194, a yes path 2196 can be followed to again block or maintain blocking the high current devices in block 2106 and the EPF power management flow diagram 2100 can be followed again. Alternatively, if no additional port finder request has been made a no path 2198 can be followed to an exit interleaving block 2166. Accordingly, the flow diagram 2100 can be used to manage power and selectively power different components of the IMD 30, including the localizer 22, separately from other high current devices, including the pump 2018 or the telemetry system of the IMD 30. Accordingly, the power management flow chart 2100 can be used, either alone or in combination with other electric circuitry systems, to provide substantially constant amplitude alternating current and/or voltage to the localizer 22. By providing substantially constant amplitude alternating current and/or voltage to the localizer 22, the localizer 22 can be used to generate a field that is substantially known and selected for allowing navigation of the delivery system 28 relative to the port 32 of the IMD 30.

Figure 7:
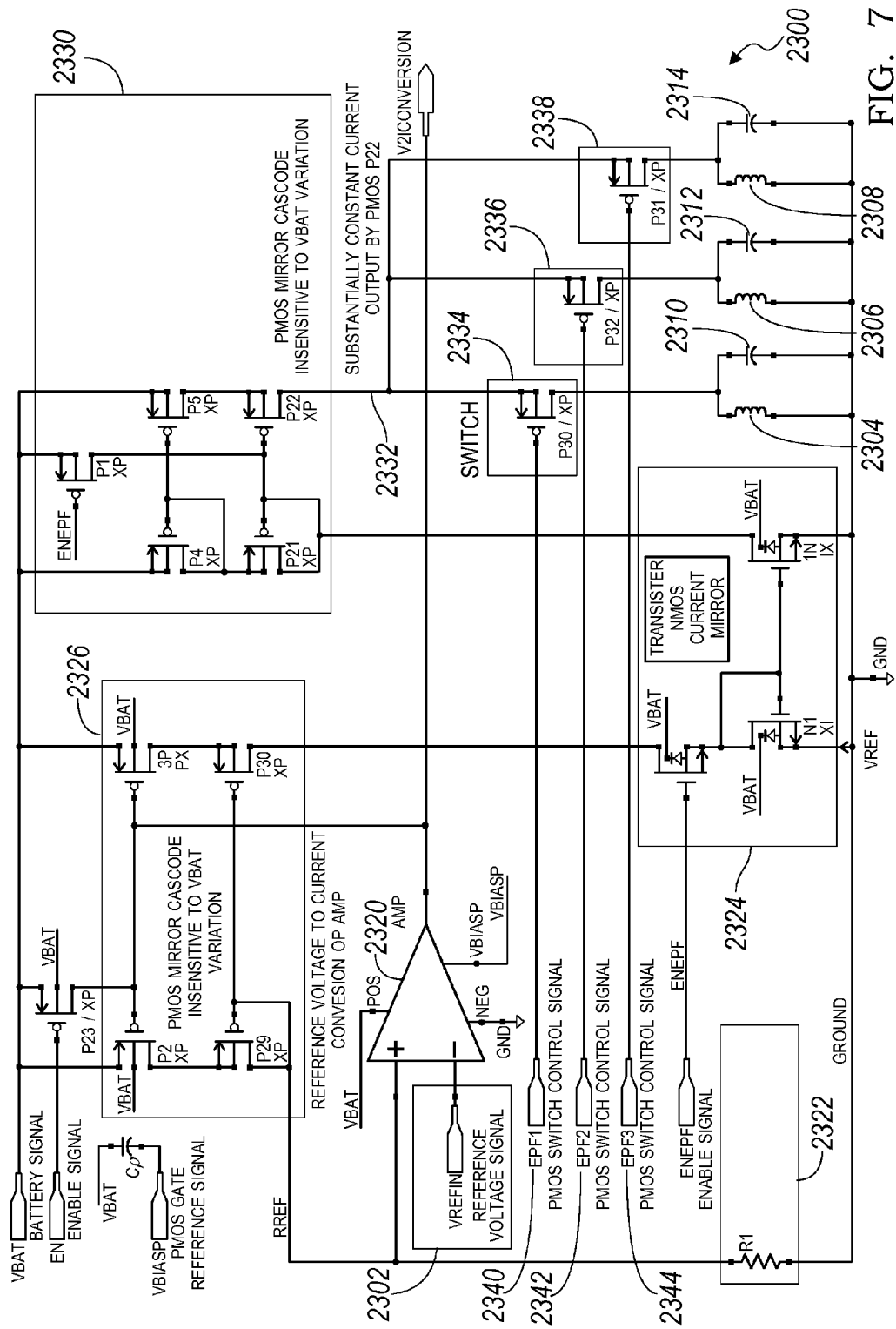
FIG. 7 is a schematic of a constant current circuit to power a transmitter coil array.

With reference to FIG. 7, a constant amplitude alternating current and/or voltage circuit 2300 illustrates connections of various components of the IMD 30 including the localizer 22 and the battery or power source 2024. The current can be a substantially constant amplitude alternating current. A substantially constant amplitude alternating current can generally vary by about 1% to about 3%, including about 1%, and further including less than about 1%. As illustrated in the circuit 2300, a voltage signal from a battery 2302 can be input into the circuit 2300 and be switched to power or drive each of the three coils, here referenced as coil 1-2304, coil 2-2306 and coil 3-2308. As discussed above, each of the coils can be provided in parallel with respective tuning capacitors including a first turning capacitor 2310, a second tuning capacitor 2312, and a third tuning capacitor 2314. It will be understood, however, as discussed above regarding the tuning circuitry, a single tuning capacitor could be provided in the system and multiple switches can be used to switch between each of the coils 2304-2308.

The reference voltage signal is applied to an operational amplifier (OP Amp) 2320 which then outputs a reference voltage to a resistor/transistor loop including a precision resistor 2322, a NMOS (e.g. a n-type transistor) transistor current mirror 2324, and a PMOS (e.g. a p-type transistor) mirror cascode 1 2326. The precision resistor 2322 can be external to components on an integrated circuit. The integrated circuit can include the OP Amp 2320, the PMOS mirror cascode 1 2326, a PMOS mirror cascode 2 2330 and the NMOS transistor current mirror 2324. The precision resistor 2322 can be substantially precise having a variance of less than about 1 percent. Additionally, the NMOS transistor current mirror 2324 can multiply a reference current by about 4 times as it is transmitted to the PMOS (e.g. p-type transistor) mirror cascode 2 2330. The PMOS mirror cascade 2 2330, along with the NMOS current mirror 2324, and the PMOS mirror cascode 1 2326 can include transistors to convert the reference voltage to a reference current that is substantially constant that is output through outputs 2332 from the PMOS mirror cascode 2 2330. The substantially constant amplitude alternating current and/or voltage can be held to vary by about 1% to about 3%, including about 1% or less, and further including a substantially immeasurable variance (e.g. a variance that is within an error of measurement).

The substantially constant amplitude alternating current and/or voltage is transmitted to the coils 2304-2308 through a plurality of respective switches. A first switch 2334 can be provided in series with the first coil 2304, a second switch 2336 can be provided in series with the second coil 2306, and a third switch 2338 can be provided in series with the third coil 2308. Additionally, as briefly mentioned above, additional switches, including three additional switches can be provided to switch the current between a single capacitor and each of the coils 2304-2308, as understood by one skilled in the art.

A signal can be provided to each of the respective switches 2334-2338 to activate the switches 2334-2338 to drive the respective coils 2304-2308. Separate control signals can be transmitted from a first PMOS switch control signal 2340, a second PMOS switch control signal 2342 and the third PMOS switch control signal 2344 to separately activate each of the three switches 2334-2338. Providing the plurality of switches 2334-2338 and the plurality of control signals 2340-2344 can allow for each of the coils 2304-2308 to be substantially independently and sequentially, or in any appropriate order, driven for generating the signal from the coils 2304-2308 of the localizer 22 for navigation of the delivery system 28.

The components of the respective portions of the circuit 2300, including the PMOS mirror cascodes and the NMOS current mirrors can be selected transistors to amplify and generate the substantially constant amplitude alternating current and/or voltage to the plurality of switches 2334-2338. Additionally, the switches 2334-2338 can be PMOS switches that are provided to switch the current to the coils 2304-2308 alternatively, for example, according to the power management flow chart 2100. In addition, the switches can be modulated to assist in tuning the frequency of the current to the coils 2304-2308. For example, as discussed above, the frequency for transmission from the coils 2304-2308 can be about 25 kHz or about 45 kHz.

III. Receiving Coil Array/Antenna Configuration

Figure 8:
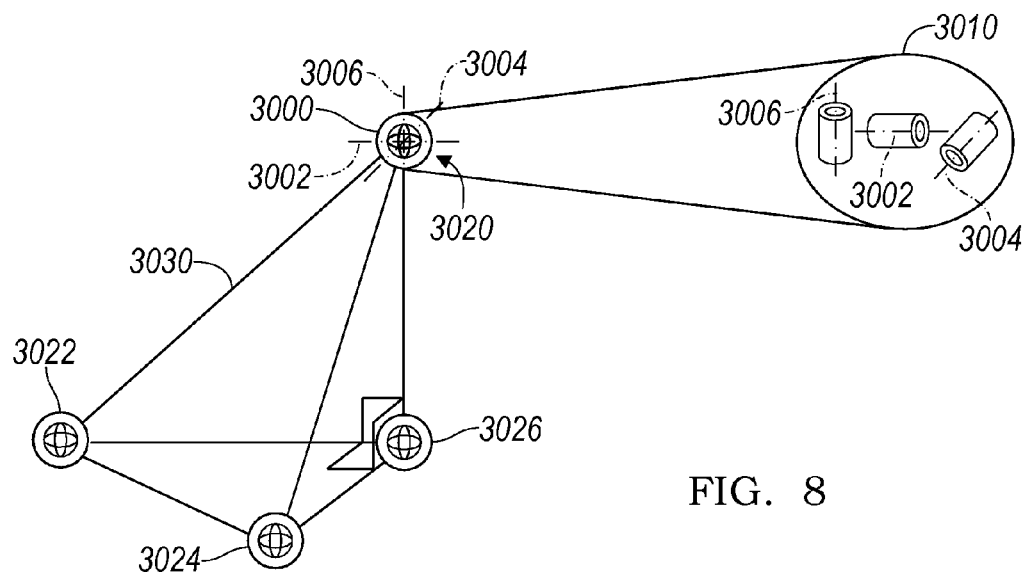
FIG. 8 is a schematic of an antenna array.

The coils of the coil array PCB 2026 can generate a field that is sensed by the antenna 24 of the tracking device. With reference to FIG. 8, the antenna portion 24 of the tracking device 20 can include one or a plurality of coils. The plurality of coils of the antenna 24 can form a receiving antenna array 24. The plurality of coils can be arrayed to receive a signal transmitted by the localizer 22 discussed above.

With reference to FIG. 8, the antenna array 24 can include a plurality of tracking devices. The tracking devices can include one or more coils. In various embodiments, the tracking devices can include a plurality of coils formed as a group, or a coil group. Each coil group can have a selected number of coils, including three coils that have a single origin 3000. Each of the coils is positioned along an x, y, and z axis 3002, 3004, and 3006, respectively.

The coils positioned around the center 3000 can be wound substantially or tightly around the single center 3000 or, alternatively, coiled to form cylinders as illustrated in alternative detail 3010 along the respective axes 3002, 3004, 3006. Accordingly, three coils are positioned around the center 3000 can form a coil group 3020. The antenna 24 can include four substantially identical coil groups including the first coil group 3020, a second coil group 3022, a third coil group 3024 and a fourth coil group 3026.

Generally, each of the coils of the coil groups 3020-3026 are wound or formed orthogonal to one another. Thus, each of the coils can determine or sense separate the field in the in the orthogonal axes and generate separate signals based on the sensed field. The separate signals from each of the coils can then be used to determine the location information regarding the location of the coil groups 3020-3026. Each of the coil groups 3020-3026 can then generally determine complete location information regarding the individual coil group 3020-3026.

Each of the coil groups 3020-3026 can be positioned substantially at the vertices of a tetrahedron 3030, as illustrated in FIG. 8. The tetrahedron can be a regular or an irregular tetrahedron. For example, the tetrahedron defined by the four coil groups can be a regular tetrahedron where the tetrahedron has substantially equal length legs or sides. Each side or leg of the tetrahedron 3030 can be about eight millimeters (mm) to about 15 mm, including about 11 mm to 14 mm, and further including about 12.5 mm. The volume of the tetrahedron, therefore, is about 200 millimeters cubed ($mm^3$) to about 300 $mm^3$, including about 250 $mm^3$. The coil groups 3020-3026 can be positioned in the tetrahedron array such that the antenna 24 includes twelve discrete coils that are formed in the tetrahedron to receive or sense the field, such as an EM field, generated by the localizer 22. It will be understood, however, that the coil groups can be formed into a selected regular or irregular geometric shape. As discussed above, however, the tetrahedron configuration can achieve a selected confidence in sensing the EM field generated by the localizer 22.

Figure 9:
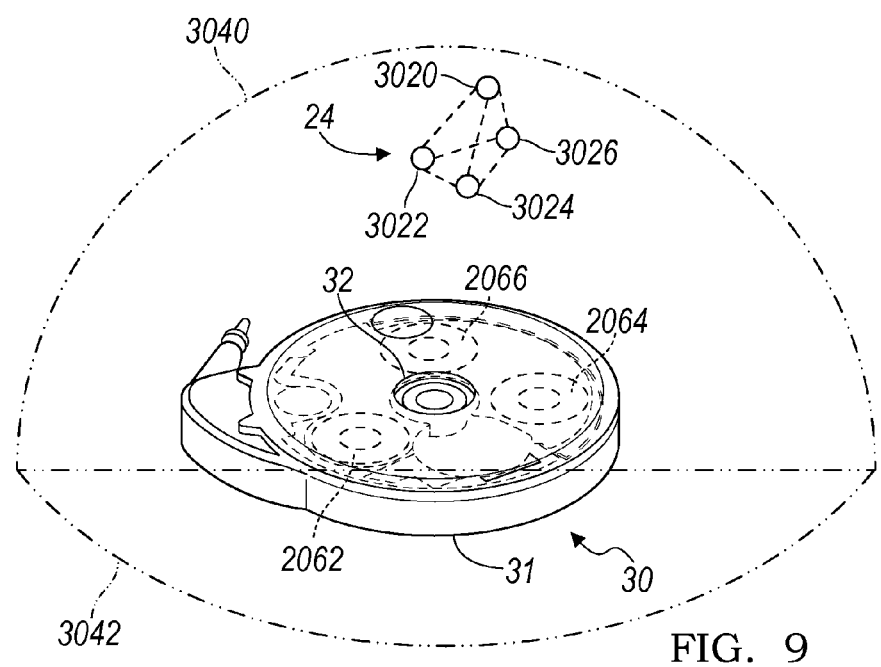
FIG. 9 is an environmental schematic view of an antenna and a transmitter coil array.

With reference to FIG. 9, the localizer 22 incorporated in the IMD 30 can include the coils on the coil PCB 2026 is illustrated by the top coils 2062-2066. The coils 2062-2066 as illustrated here and in the Figs above, are generally positioned around the area of the port 32. It can be selected to place the coils at a selected spacing or substantially evenly spaced apart. These coils 2062-2066, when powered as discussed above, can generate a navigation field that is or can include the EM field that can be generated or emitted into the space surrounding by the IMD 30 as illustrated by the hemispherical region 3040, generally around the port 32 as well. It will be understood that the navigation region 3040 can be divided into various navigation zones, as discussed further herein, relative to the implanted medical device 30. In addition, the navigation region 3040 can be any appropriate shape formed by the localizer 22 relative to the implanted medical device 30. For example, the components or materials of the implanted medical device 30 can affect the shape of the field that forms the navigation region 3040. As illustrated, however, the substantially planar shape of the coils of the localizer 22 in the implanted medical device 30 can form a substantially spherical or hemispherical navigation region relative to the port 32 of the implanted medical device 30. Also, the coils 2062-2066 can generate a small or weak portion of a field 3042, which may be smaller or weaker than the general navigation field 3040, that extends to an under or bottom side 31 of the IMD 30. The smaller field portion 3042 can be used to determine the orientation of the IMD 30 relative to the antenna 24, as discussed herein.

Once the antenna 24 is positioned within the navigation region 3040 of the implanted medical device 30, the position of the antenna 24 can be determined with the navigation system 10, including the processor 12. The tracking device 20 can communicate via wires or wirelessly with the processor 12. Similarly, the processor 12 can communicate wirelessly or via wires with the localizer 22 of the IMD 30. Various transmission systems are discussed in the patents and applications incorporated herein by reference and via the systems discussed above. Further, the programmer 2027 can transmit via wires or wirelessly with the navigation system 10 and with the IMD 30.

The determination of the location of the antenna 24 can be based upon navigation techniques by determining the sensed field in each of the coils of the coil groups 3020-3026 in the antenna array 24. Because each of the coil groups 3020-3026 includes three coils that are positioned substantially orthogonal to each other (e.g. one along each of the three dimensions of space) in the navigation region 3040 substantially all location information can be determined. By providing the four coil groups at spaced positions from one another along the legs 3030 of the tetrahedron, a three-dimensional location, including X-Y-Z spatial coordinates and orientation of each of the coil groups 3020-3026 can be determined. Each of the coil groups 3020-3026 can then be interpolated or the information can be used to determine the position of the portion of the tetrahedron defined by the coil groups 3020-3026 of the antenna 24. The position can then be illustrated on the display 14 as discussed further herein to provide information to a user for moving the delivery system 28 to the port 32.

The localizer 22, including the plurality of coils formed by the coil parts 2042, 2062; 2044, 2064; and 2046, 2066 that generate the navigation region 3040 and the antenna 24 including the coil groups 3020-3026, can be used to guide the delivery system 28 to the port 32 of the IMD 30. As discussed briefly above, and in further detail herein, the antenna 24 associated with the delivery system 28 can be used alone with the localizer 22 incorporated into the IMD 30 to navigate the delivery system 28 to the IMD 30 for filling the reservoir 34 of the IMD 30. Accordingly, the localizer 22, incorporated in the IMD 30 and the antenna 24 included with the delivery system 28, can be used to provide a substantially mobile and discrete system that can be used to fill the reservoir 34 by navigating the needle 4058 to the port 32. For example, the delivery system 28, as discussed further herein, can be a portable system that includes the navigation processor 12, display 14, and the antenna 24 that can be used in a Doctor's office or other substantially non-surgical outpatient or clinical setting. This allows for filling the reservoir 34 of the IMD 30 without requiring large or complex external navigation systems to identify the location of the port 32 and the relative position of the delivery system 28 for filling the reservoir 34.

It will be further understood that the antenna 24 can be operated to generate a field that is sensed with the coils of the localizer 22 in the IMD 30. Thus, rather than the localizer 22 generating the EM field 3040 in the navigation space, the localizer 22 can sense an EM field being generated by the antenna array 24. Otherwise, the navigation system can be operated in a similar manner to power the coils of the localizer 22 to receive the EM field generated by the antenna 24.

IV. Supply System and Support Guide

The delivery system 28 can be a substantially efficient system to deliver the functional fluid to the reservoir 34 of the IMD 30. The tracking device 20 can be associated with the delivery system 28 to allow navigation of the delivery system 28 relative to the IMD 30. Because the IMD 30 has been implanted in the patient 16 for a period of time, the delivery system 28 can be navigated to the precise location of the port 32 using the tracking device 20. As discussed above and as shown in FIG. 1, the tracking device 20" can be operably coupled to the supply assembly 50 such that supply assembly 50 is the tracked instrument 61", and/or the tracking device 20 can be operably coupled to the support tool 60 such that the support tool 60 is the tracked instrument 61.

Figure 10:
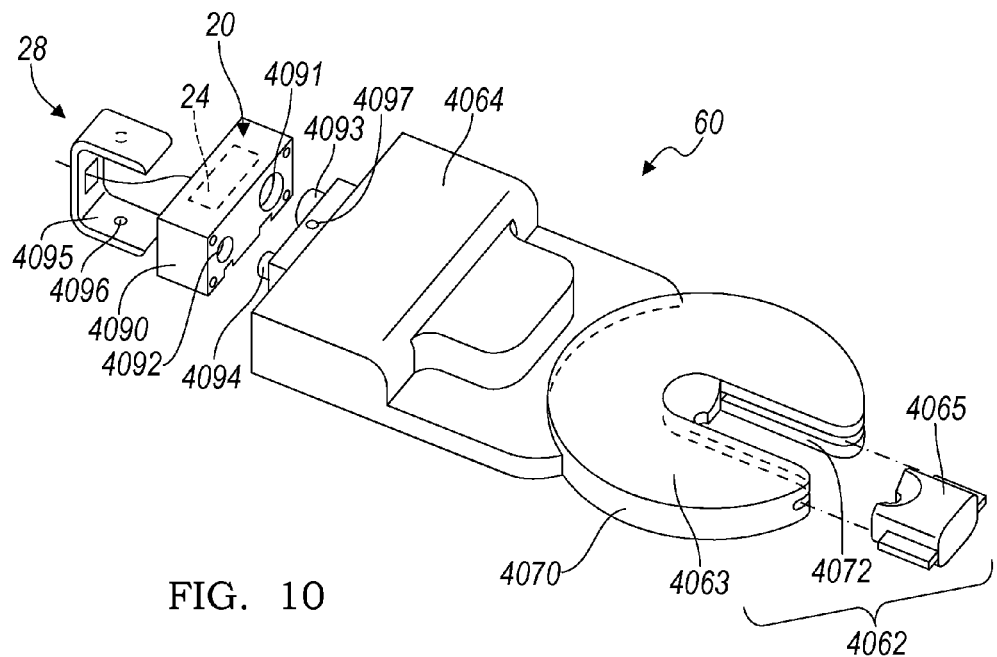
FIG. 10 is an exploded, perspective view of a support tool of the delivery system according to various exemplary embodiments of the present disclosure.
Figure 11:
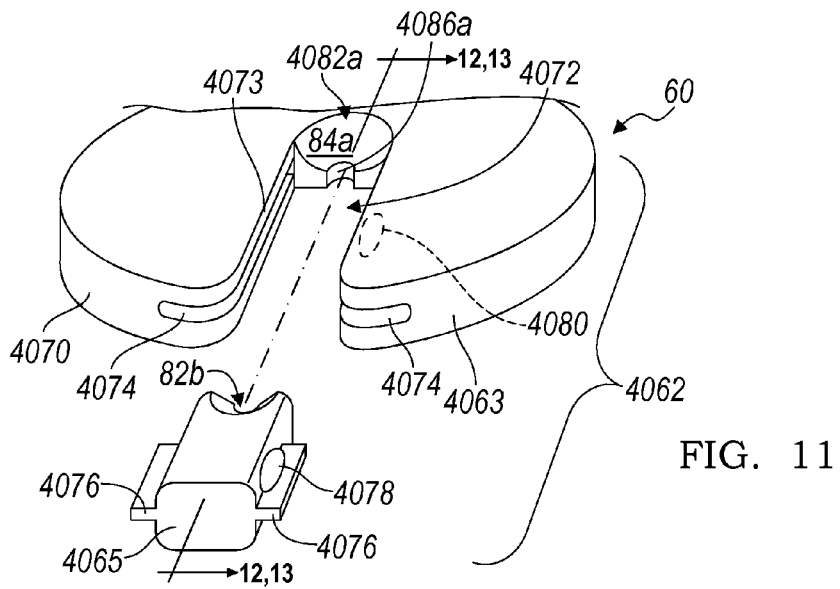
FIG. 11 is an exploded view of the support tool of FIG. 10.
Figure 12:
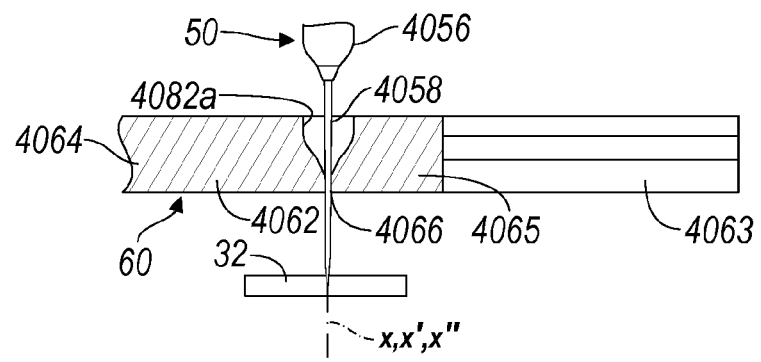
FIG. 12 is a section view of the support tool of FIG. 10.
Figure 13:
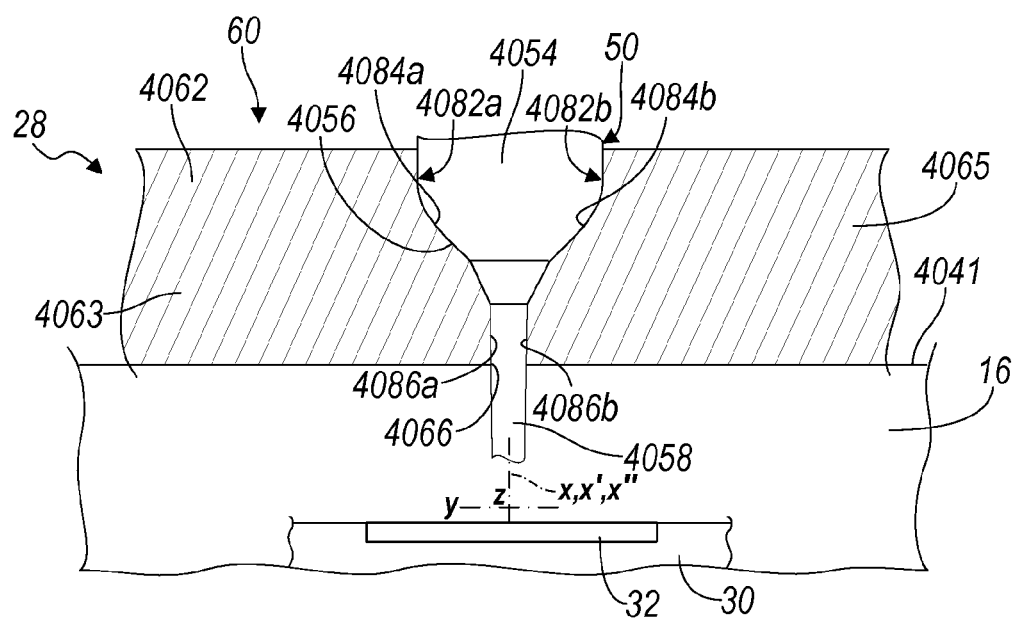
FIG. 13 is a section view of the support tool of FIG. 10.

Referring now to FIGS. 1 and 10-13, the delivery system 28 will be discussed in greater detail. As shown in FIGS. 1, 12, and 13, the supply assembly 50 can incorporate various features of a commercially available hypodermic needle or syringe. As such, the supply assembly 50 can include a hollow container 4054 with a curved outer surface 4056 (e.g., three dimensionally curved outer surface 4056). The supply assembly 50 can also include a piercing member 4058 or needle that is elongate and that has a sharpened distal tip 4059 for piercing the skin of the patient 16. The piercing member 4058 can define a longitudinal axis X' (i.e., a supply axis), and a lumen (not shown) can extend longitudinally from the container 4054 and axially through the piercing member 4058. The supply assembly 50 can also include a plunger (not shown) that is moveably coupled to the container 4054 to be manually or automatically actuated by the user in order to force the functional fluid from the supply assembly 50. Thus, as will be discussed, when in a target position relative to the port 32 of the implantable device 30, the piercing member 4058 can pierce the skin 4041 of the patient 16 (FIG. 13) to be received by the port 32, and the functional fluid can be delivered from the supply assembly 50 to the reservoir 34 of the implantable device 30.

Figure 26:
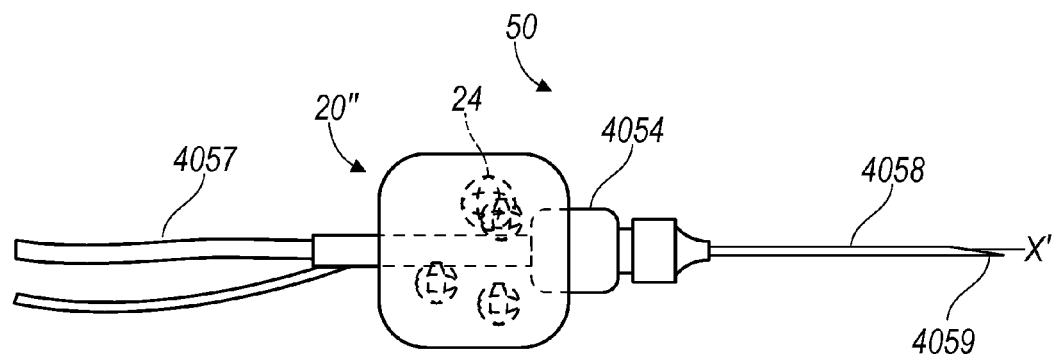
FIG. 26 is a side view of a supply assembly according to various other exemplary embodiments of the present disclosure.
Figure 27:
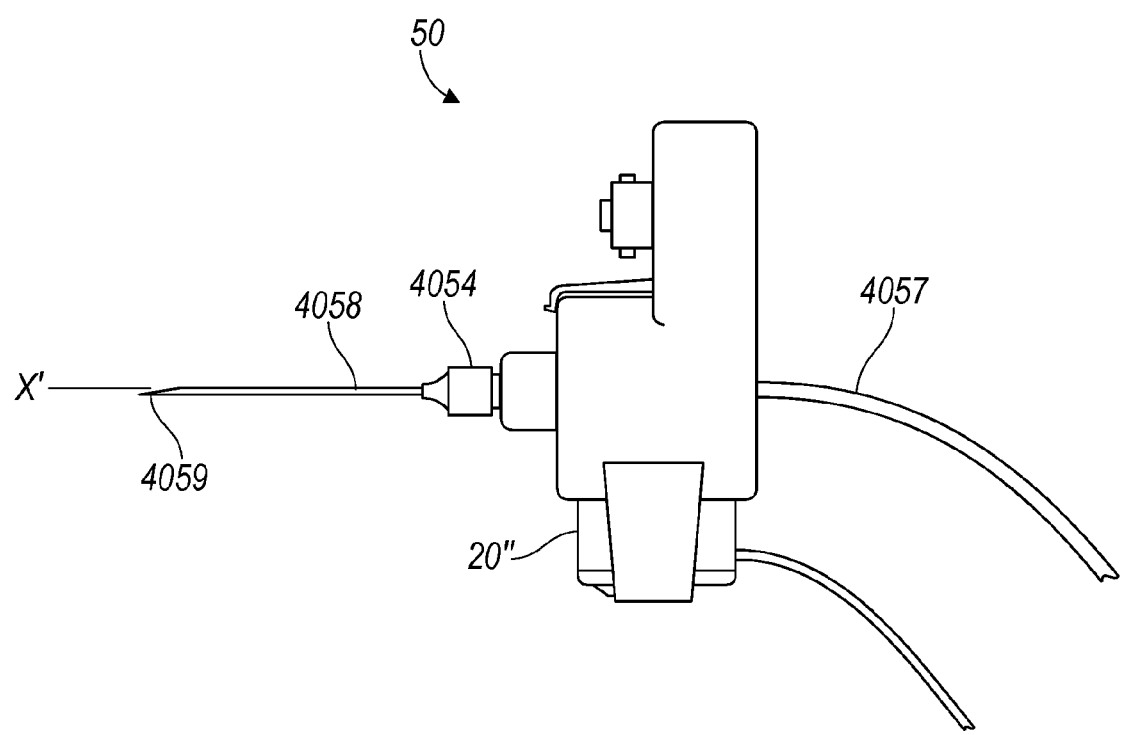
FIG. 27 is a side view of a supply assembly according to various other exemplary embodiments of the present disclosure.

In other embodiments illustrated in FIGS. 26 and 27, the container 4054 can be operably coupled to a supply line 4057 (e.g., a tube or hose) on one end. The supply line 4057 can supply the functional fluid through the container 4054 to the piercing member 4058. Accordingly, the functional fluid can be delivered conveniently by pumping the functional fluid through the supply line 4057.

Referring now to FIGS. 1, 10 and 11, the support or guide tool 60 will be discussed in greater detail. As shown, the support tool 60 can be substantially flat and thin and can be made out of a rigid material, such as a polymeric material. The support tool 60 can include a support member 4062 and a handle 4064. The handle 4064 can be elongate and can be sized such that the user can grasp and support the handle 4064 with one hand or with a few fingers. The support member 4062 can be wider than the handle 4064, and the handle 4064 can extend away from the support member 4062.

The support member 4062 can include a main body 4063 and a removable member 4065 (FIGS. 10-13). The main body 4063 can be integrally connected to the handle 4064 so as to be monolithic. The removable member 4065 can be removably attached to the main body 4063 as will be discussed in greater detail below.

The support member 4062 can also include an opening 4066 with an axis X" (FIGS. 12 and 13). As shown in FIGS. 12 and 13, the opening 4066 can be cooperatively defined by both the main body 4063 and the removable member 4065. As will be discussed in greater detail below, the opening 4066 can receive the supply assembly 50 (FIGS. 12 and 13), and the support member 4062 (i.e., both the main body 4063 and the removable member 4065) can support the supply assembly 50 such that the axis X' of the supply assembly 50 remains substantially fixed relative to the axis X" of the support member 4062. In some embodiments, the support member 4062 can support the supply assembly 50 such that the axis X' of the supply assembly 50 remains substantially aligned with and fixed relative to both the axis X" of the support member 4062 and the axis X of the port 32. Accordingly, the support member 4062 can hold the supply assembly 50 with the axes X, X', X" substantially aligned to ensure that the supply assembly 50 engages the port 32 as will be discussed.

As shown in FIG. 10, the main body 4063 can include an outer edge 4070 and an elongate slot 4072 that extends from the outer edge 4070. As will be discussed, the slot 4072 defines a portion of the opening 4066 that receives the supply assembly 50. Also, as shown in FIG. 11, the main body 4063 can include grooves 4074 recessed on inner surfaces 4073 of the slot 4072. The grooves 4074 can extend substantially parallel to the slot 4072.

Also, as shown in FIG. 11, the removable member 4065 can be generally cruciform in shape so as to include tongues 4076 extending from opposite sides of the removable member 4065. Each of the tongues 4076 can be slideably received within respective ones of the grooves 4074 so as to removably attach the removable member 4065 to the main body 4063. Accordingly, the removable member 4065 can be removably attached to the main body 4063 via a tongue and groove coupling.

It will be appreciated that the tongues 4076 could be included on the main body 4063, and the grooves 4074 could be included on the removable member 4065 without departing from the scope of the present disclosure. It will further be appreciated that the removable member 4065 could be removably attached to the main body 4063 via any other suitable coupling. For instance, the removable member 4065 could be attached via a break-away coupling. More specifically, the tongues 4076 could be fixed within the respective grooves 4074, and in order to remove the removable member 4065 from the main body 4063, the user can fracture and break the tongues 4076 away from the removable member 4065 by hand.

As shown in FIG. 11, the removable member 4065 can also include a projection 4078 that is received in a corresponding recess 4080 (shown in phantom) on the main body 4063. The projection 4078 can be a nub of raised material that is located on one or more of the tongues 4076, and the recess 4080 can be included within one or more of the grooves 4074. However, it will be appreciated that the projection 4078 can be included on the main body 4063, and the recess 4080 can be included on the removable member 4065. The projection 4078 can be received within the recess 4080 in order to retain the removable member 4065 in a substantially fixed position relative to the main body 4063. For instance, as the tongues 4076 advance into the respective grooves 4074, the projection 4078 can eventually snap into the recess 4080 to substantially lock the removable member 4065 in a fixed position. Thus, the position of the removable member 4065 relative to the main body 4063 can be ensured.

As shown in FIGS. 12 and 13, the main body 4063 and the removable member 4065 can each include a nesting surface 4082a, 4082b. With the nesting surfaces 4082a, 4082b, the removable member 4065 and the main body 4063 can cooperatively support the supply assembly 50. More specifically, the nesting surfaces 4082a, 4082b can be three dimensionally contoured so as to substantially conform in shape and contour with the corresponding outer surface 4056 of the supply assembly 50. The nesting surfaces 4082a, 4082b can each include an upper portion 4084a, 4084b and a lower portion 4086a, 4086b (FIG. 13). The upper portions 4084a, 4084b can be recessed deeper than the lower portions 4086a, 4086b. Also, the upper portions 4084a, 4084b can be three-dimensionally contoured, and the lower portion 4086a, 4086b can be two-dimensionally contoured.

Thus, when the supply assembly 50 is inserted into the opening 4066 (FIG. 13), the upper portions 4084a, 4084b can closely abut and nest against the outer surface 4056 of the container 4054 of the supply assembly 50. Also, the lower portions 4086a, 4086b can closely abut and nest against the piercing member 4058.

Such nesting maintains alignment between the axis X' of the supply assembly 50 and the axis X" of the opening 4066 of the support tool 60, and the support tool 60 can help the user to maintain the supply assembly 50 in its target alignment relative to the axis X of the port 32 of the implantable device 30. For instance, the support tool 60 can limit rotational movement of the axis X' of the supply assembly 50 relative to axes Y, Z as shown in FIG. 13.

It will be appreciated that the nesting between the supply assembly 50 and the support tool 60 can be especially effective because the opening 4066 is substantially continuous so as to extend substantially continuously about the axis X' of the supply assembly 50. More specifically, the main body 4063 and the removable member 4065 (and the nesting surfaces 4082a, 4082b) cooperate to substantially completely surround the supply assembly 50 for ensuring alignment between the axes X, X', X. However, it will be appreciated that the opening 4066 could be discontinuous (e.g., the removable member 4065 might not be included and the notch 4072 would remain open) without departing from the scope of the present disclosure.

As stated, the lower portion 4086*a*, 4086*b* of the nesting surfaces 4082*a*, 4082*b* closely conform in shape to the piercing member 4058 of the supply assembly 50. For instance, the lower portions 4086*a*, 4086*b* can be spaced apart substantially equal to the diameter of the piercing member 4058. As such, even when the container 4054 of the supply assembly 50 is spaced from the upper portion 4084*a*, 4084*b* of the nesting surfaces 4082*a*, 4082*b* (FIG. 12), the lower portion 4086*a*, 4086*b* of the nesting surfaces 4082*a*, 4082*b* can maintain alignment between the axis X' of the supply assembly 50 and the axis X" of the opening 4066 of the support tool 60. Thus, for instance, if the port 32 of the implantable device 30 is just below the surface of the skin 4041, the supply assembly 50 can pierce shallowly through the skin 4041, and the support tool 60 can maintain the supply assembly 50 in its target alignment.

Once the supply assembly 50 has engaged the port 32 of the implantable device 30 (FIGS. 12 and 13), the removable member 4065 can be selectively removed from the main body 4063 as discussed above. Then, the main body 4063 can be moved away from the patient 16 while the supply assembly 50 remains in a substantially fixed position relative to the patient 16 (i.e., remains engaged with the port 32). More specifically, by removing the removable member 4065, the main body 4063 can move away from the patient until the supply assembly 50 is fully outside the slot 4072. Then, the support tool 60 can be re-used for another patient 16, or the support tool 60 can be discarded.

In some embodiments, the support tool 60 can be packaged with the removable member 4065 already attached to the main body 4063. However, in other embodiments, the support tool 60 and the removable member 4065 can be packaged separately. Moreover, the supply assembly 50 and the support tool 60 can be packaged together or separately. Additionally, in some embodiments, the member 4065 is not removable and is instead integrally connected to the main body 4063 so as to be monolithic.

Referring now to FIG. 10, the tracking device 20 of the navigation system 10 will be discussed in greater detail. The tracking device 20 can include one or more antennae 24 that are housed within a housing 4090. The housing 4090 can be operably coupled to the support tool 60 at a known position and orientation relative to the opening 4066 and the axis X" of the opening 4066. Thus, the navigation system 10 can communicate with the antennae 24 and the localizer 22 (FIG. 1) in order to detect the location of the axis X" of the opening 4066 relative to the axis X of the port 32 of the implantable device 30. Since the support tool 60 maintains the axis X' of the supply assembly 50 in alignment with the axis X" of the opening 4066, the tracking device 20 can detect the location and orientation of the axis X' of the supply assembly 50 relative to the axis X of the port 32.

As shown in FIG. 10, the tracking device 20 can be removably coupled to the support tool 60. For instance, the housing 4090 of the tracking device 20 can be removably coupled to the handle 4064 on an end opposite the support member 4062. In some embodiments, the housing 4090 and the handle 4064 are coupled via a one-way coupling. More specifically, the housing 4090 can include a first recess 4091 and a second recess 4092, and the first recess 4091 can be larger in diameter than the second recess 4092. Also, the handle 4064 can include a first projection 4093 and a second projection 4094, which correspond in size and which are received in the first and second recesses 4091, 4092, respectively. Accordingly, the tracking device 20 can be keyed to the handle 4064 and attached to the handle 4064 in only one relative orientation, thereby ensuring that the antenna 24 is at a known position/orientation relative to the opening 4066 and the supply assembly 50.

The tracking device 20 can further include a retainer clip 4095 that extends around the housing 4090 and removably attaches to the handle 4064 of the support tool 60. The retainer clip 4095 can include one or more recesses 4096 that receive corresponding projections 4097 included on the handle 4064 of the support tool 60. As such, the retainer clip 4095 can further secure the housing 4090 to the handle 4064, and the position/orientation of the antenna 24 relative to the opening 4066 and supply assembly 50 can be further ensured.

Figure 25:
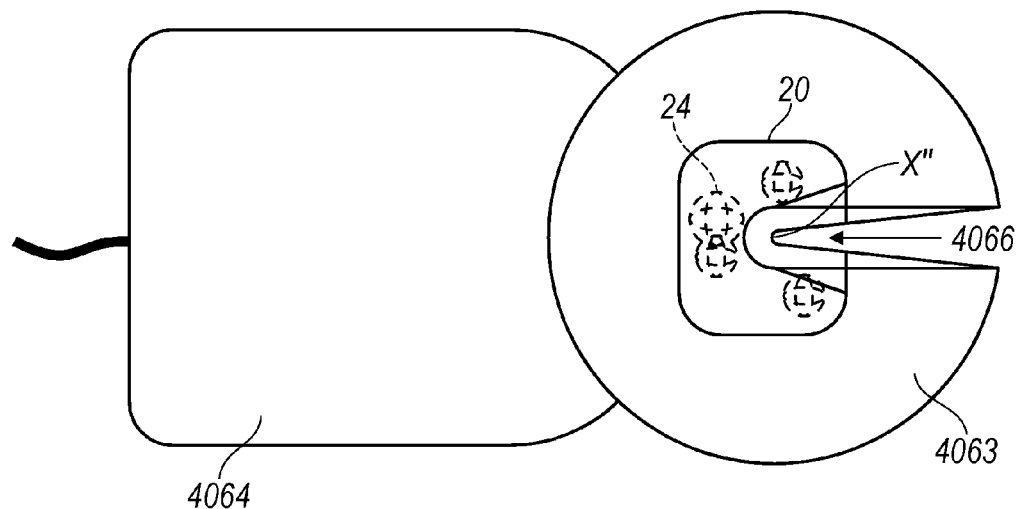
FIG. 25 is a top view of a support tool according to various other exemplary embodiments of the present disclosure.

In other embodiments illustrated in FIG. 25, the tracking device 20 can be integrally or removably coupled to main body 4063 of the support tool 60. As shown, the antenna 24 can be disposed about the axis X" (e.g., in a tetrahedral configuration) and adjacent the opening 4066. The tracking device 20 can be coupled in any suitable manner, including the means of attachment described above with respect to FIG. 10.

It will be appreciated that because the tracking device 20 is removably attached to the support tool 60, the tracking device 20 can be used multiple times with multiple patients 16. This can produce cost savings because the relatively expensive tracking device 20 can be re-used while the less expensive support member 4062 and handle 4064 can be discarded. Also, there is a reduced chance of cross contamination between patients 16 because the support member 4062 and handle 4064 can be used a single time on one patient 16. This becomes important since the support member 4062 and the handle 4064 are likely to contact the skin 4041 and become contaminated by blood, tissue, germs, etc.

Also, because the support tool 60 is tracked, the support tool 60 can be used for other purposes. For instance, the support tool 60 can used while preparing to supply the functional fluid, independent of the supply assembly 50. The support tool 60 can be laid against the patient 16 to find the position of the support tool 60 relative to the port 32 of the IMD 30. Also, as will be discussed in greater detail below, this information can be used to automatically detect and indicate the type of piercing member 4058 needed for supplying the functional fluid to the port 32. For instance, with the detected position of the support tool 60 relative to the port 32, the system can detect the necessary length of the piercing member 4058, etc.

Moreover, as mentioned above, the tracking device 20" (shown in phantom in FIG. 1 and in solid lines in FIGS. 26 and 27) can be operably coupled directly to the supply assembly 50 at a known location relative to the distal tip 4059 of the piercing member 4058. For instance, as shown in FIG. 26, the tracking device 20" can be removably coupled to the container 4054 of the supply assembly 50. Also, as shown in FIG. 26, the tracking device 20" can include antenna 24 that are disposed about the supply axis X' (e.g., in a tetrahedral configuration). In other embodiments shown in FIG. 27, the tracking device 20" can be removably coupled to the container 4054 of the supply assembly 50 (e.g., via a Luer Lock connection or via any other suitable connection) such that the tracking device 20" is disposed entirely on one side of the supply axis X'. Also, in some embodiments, the tracking device 20" can be keyed to the supply assembly 50 such that the tracking device 20" is at a known orientation relative to the supply assembly 50 when attached thereto. In other embodiments, the tracking device 20" can be integrally coupled to the supply assembly 50.

It will be appreciated that the tracking device 20" can be coupled to the supply assembly 50 in any suitable location and in any suitable manner. Furthermore, it will be appreciated that the tracking device 20" can be coupled to the supply assembly 50 as disclosed in U.S. Patent Application Publication No. 2009/0082782, published Mar. 26, 2009, to Scott Kalpin, which is incorporated herein by reference in its entirety.

Thus, in some embodiments, the distal tip 4059 of the piercing member 4058 can be tracked independent of the support tool 60. Also, where the tracking device 20" is removably coupled to the supply assembly 50, the supply assembly 50 (or at least the piercing member 4058) can be used once and discarded, and the more expensive tracking device 20" can be removed from the supply assembly 50 for repeated use.

Furthermore, in some embodiments, the tracking device 20" can be coupled to the container 4054 of the supply assembly 50 and used independent of the piercing member 4058. For instance, the tracking device 20" can detect the relative position of the container 4054 relative to the port 32 of the IMD 30. Then, as will be discussed below, the system can automatically detect the length of the piercing member 4058 necessary to reach the port 32.

Figure 14:
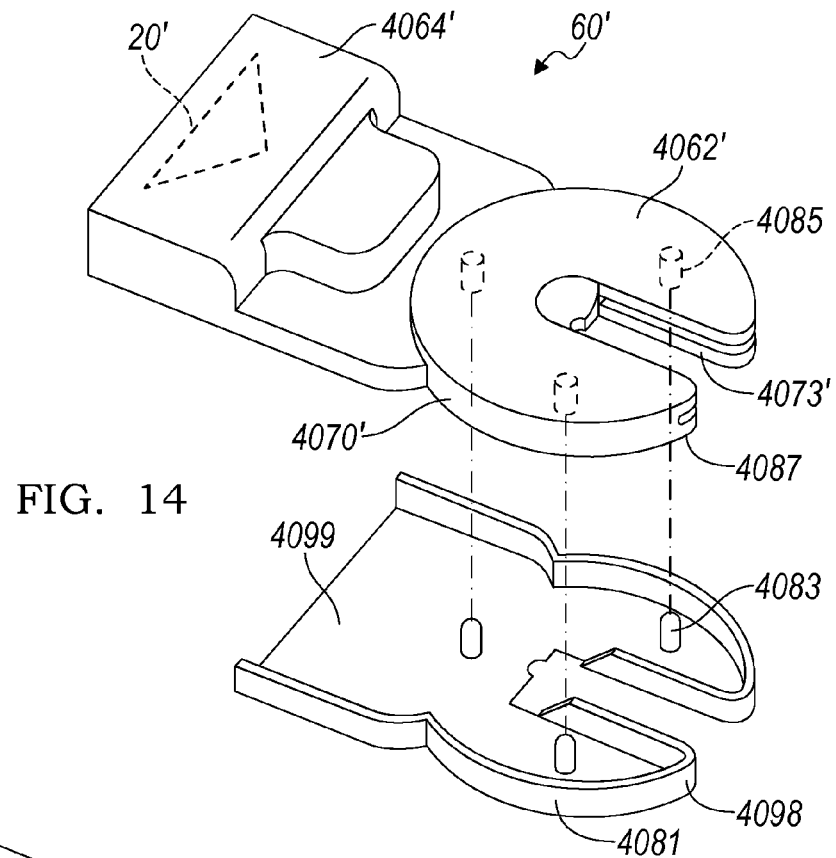
FIG. 14 is an exploded, perspective view of the support tool according to additional exemplary embodiments of the present disclosure.

As shown in FIG. 14, the support tool 60' can also include a prophylactic member 4098. The prophylactic member 4098 can be made out of any suitable material, such as a substantially rigid polymer. The prophylactic member 4098 can include a base 4099 and a wall 4081 that extends from an outer edge of the base 4099. The prophylactic member 4098 can also be forked so as to have a shape substantially similar to the support member 4062'. The prophylactic member 4098 can also include one or more projections 4083 that extend from an interior portion of the base 4099 in the same direction as the wall 4081.

The projections 4083 can be removably received within corresponding recesses 4085 formed in a bottom surface 4087 of the support member 4062'. In some embodiments, the projections 4083 can be held within the recesses 4085 via a frictional fit. In other embodiments, the projections 4083 can be held within the recesses 4085 via an interference fit. It will also be appreciated that the support member 4062' can include the projections 4083 while the prophylactic member 4098 can include the recesses 4085.

When attached, the base 4099 can cover the bottom surface 4087 of the support member 4062', and the wall 4081 can cover the outer edge 4070' and the inner surface 4073' of the support member 4062'. Also, during use, the prophylactic member 4098 can be disposed between the support member 4062' and the patient to thereby reduce the likelihood of contamination of the support member 4062'. Moreover, the prophylactic member 4098 can be disposed between the supply assembly (not shown in FIG. 14) and the support member 4062'. Also, although a removable member 4065 of the type shown in FIG. 10 is not shown in FIG. 14, the prophylactic member 4098 can be shaped so as to fit over the removable member 4065 as well.

Thus, the support tool 60' can be sterilized and used multiple times with multiple different patients because contamination of the support member 4062' is unlikely. Also, the prophylactic member 4098 can be discarded after use, and a new, sterile prophylactic member 4098 can be used for each patient. Thus, the prophylactic member 4098 can be useful in cases where the tracking device 20' is fixedly attached to the support tool 60'. However, it will be appreciated that the prophylactic member 4098 can be used in cases where the tracking device 20' is removably attached as well.

Figure 15:
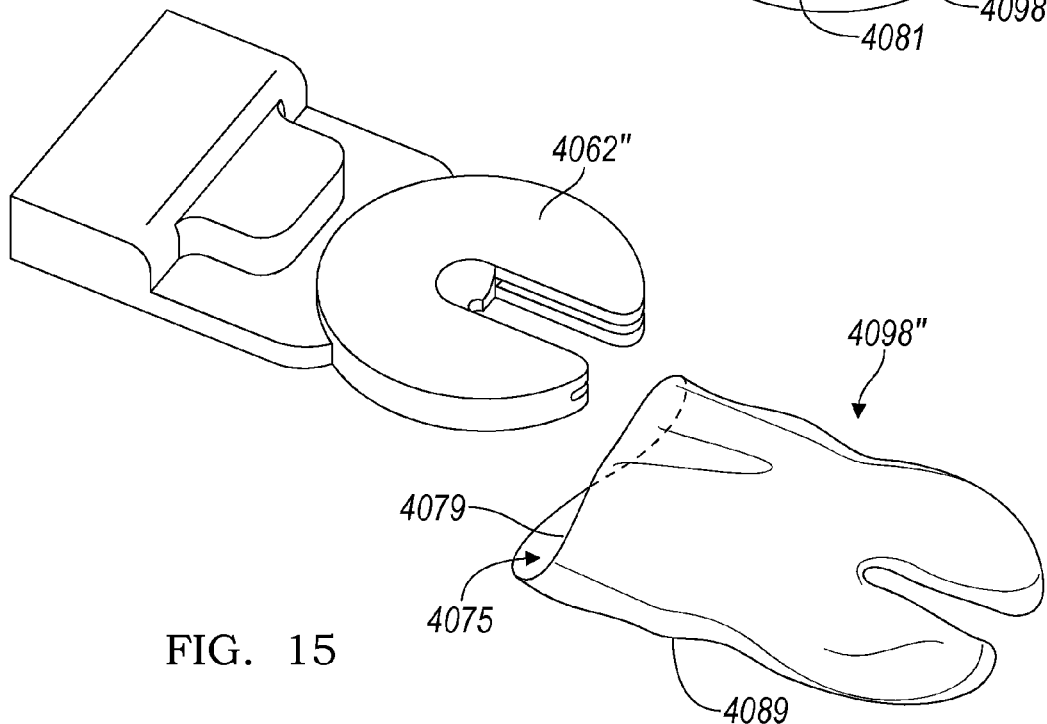
FIG. 15 is an exploded, perspective view of the support tool according to additional exemplary embodiments of the present disclosure.

Referring now to FIG. 15, another embodiment of the prophylactic member 4098" is illustrated. In the embodiment shown, the prophylactic member 4098" includes a glove portion 4089 with an opening 4079. The glove portion 4089 can be made out of any suitable material, such as a relatively thin layer of flexible and elastic polymeric material. The opening 4079 can be sized so as to receive the support member 4062" such that the support member 4062" can be disposed in an interior space 4075 of the prophylactic member 4098".

Accordingly, during use, the support member 4062" can be substantially enclosed within the interior space 4075 of the prophylactic member 4098", and the prophylactic member 4098" can act as a barrier between the patient and the support member 4062" as well as a barrier between the supply assembly (not shown in FIG. 15) and the support member 4062". Thus, the prophylactic member 4098" can reduce the likelihood of contamination of the support member 4062".

V. Navigation Display

The localizer 22 and the tracking device 20, as discussed above, can be provided in the IMD 30 and the delivery system 28, respectively, to allow navigation of the delivery system 28 relative to the port 32 of the IMD 30. Once navigated the delivery system 28 can be used to deliver the functional fluid to the reservoir 34 of the IMD 30. The display 14 of the navigation system 10 can be used to graphically display a rendered image illustrating the determined location of the delivery system 28 either alone or with information relating to the position of the IMD 30.

Referring now to FIGS. 16-24, a system and method for displaying guidance or navigation information and navigating the tracked instrument 61, 61" will now be discussed in greater detail according to various embodiments of the present disclosure. As discussed above, the navigation system 10 can detect the location of the tracked instrument 61, 61" relative to the implantable device 30. For instance, the navigation system 10 can detect the location of the port 32 and/or the insertion axis X relative to the tracked instrument 61, 61", and with this information, the user can more easily locate tracked instrument 61, 61" relative to the port 32 for delivering the functional fluid to the reservoir 34. To facilitate navigation of the tracked instrument 61, 61", the processor system 12 can cooperate with the tracked instrument 61, 61", implantable device 30 and display device 14 to provide guidance information as well as an interactive user interface, as will be described in greater detail below. The following discussion will continue to make reference to the tracked instrument 61, 61", where, as discussed above, the tracked instrument 61 can include support tool 60 with operably coupled tracking device 20 and supply assembly 50, and the tracked instrument 61" can include supply assembly 50 with the removably coupled tracking device 20".

Typically, a medical practitioner, such as a nurse or clinician (hereinafter referred to as a "user"), can palpate the patient 16 to determine a general or approximate location of the implantable device 30 to be filled with the functional fluid. After determining the approximate location, the user can use the navigation system 10 to provide general and detailed guidance information to navigate the tracked instrument 61, 61" to the location of the port 32. The navigation system 10 can be a portable system where processor system 12 and display device 14 are incorporated therein for portable use, or can be a permanent or semi-permanent system incorporated into a facility room or on a movable workstation (not shown).

Figure 16:
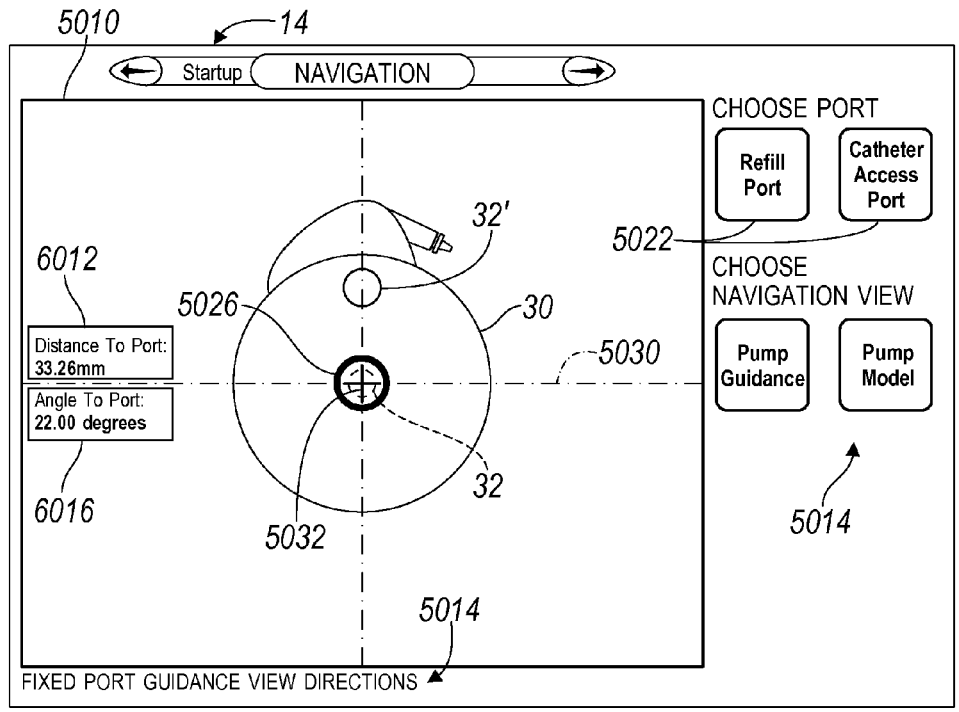
FIG. 16 is an exemplary view of a display device according to various exemplary embodiments of the present disclosure.

The display device 14 can include an image area or graphical display 5010 for displaying guidance information and receiving user input, as well as a menu or instruction area or areas 5014 that can be used to display various instructions, menus, prompts and the like for communicating with and receiving input from the user via the processor 12. The user can turn on or initialize the navigation system, upon which the processor system 12 can cooperate with the display device 14 to show the imageable area 5010 and instruction area 5014, as generally shown in FIG. 16. Once initialized, the display device 14 can prompt the user to select from a preconfigured menu of various implantable devices 30.

As the navigation system 10 can be used with various implantable devices 30, selection of a certain implantable device 30 can be used to upload specific information related to that specific device, including but not limited to, a graphical illustration of the device, calibration information, port 32 location relative to the localizer 22, and a number of ports in the pump as well as the function of each port. For example, and with reference to an implantable device 30 having multiple ports, the exemplary implantable device 30 can be configured with two ports 32, shown as 32 and 32' in FIG. 16, where port 32 can be used to fill reservoir 34 as previously discussed, and port 32' can be use for direct injection of the functional fluid to a portion of the anatomy.

In an alternative configuration, the display device 14 can be automatically initialized using the telemetry system discussed above. In this configuration, data regarding the implantable device 30, such as model, number of ports, calibration data, etc. can be communicated to the processor system 12 and display device 14 using the telemetry system such that the user would not need to initialize the system and select the implantable device model.

If an implantable device 30 model is selected by the user or communicated by the telemetry system that includes multiple ports, the processor system 12 can display the multiple ports on display device 14 and prompt the user to select a target port (i.e., port 32 or 32') for navigation thereto, via port selection prompts 5022. The selected target port 32 or 32' can be identified on display device 14 with a graphical representation, such as ring 5026. Once an implantable device model is selected and a target port is selected, if applicable, the view of the image area can be centered on the selected target port and a view direction of the image area can be parallel to the insertion axis X of the target port, as shown in FIGS. 16-23. In this manner, the view shown on the image area 5010 can be perpendicular to the insertion axis X of port 32 such that axis X is normal to the paper in FIGS. 16-17.

Ring 5026 can be illustrated with a specific color and size to differentiate ring 5026 from other guidance rings that will be discussed in greater detail below. It should also be appreciated that ring 5026 can be illustrated in various geometric patterns or configurations suitable to visually identify the selected target port 32 or 32'. Once a port is selected, such as port 32 in FIG. 16, the processor system can display a crosshair configuration 5030 with a graphical representation of an origin or target location 5032 over the selected port 32, as shown for example in FIG. 16. For discussion purposes, port 32 will hereinafter be referred to as the selected or target port 32.

Upon initializing the navigation system 10 and selecting an implantable device model, the user can calibrate the display device 14 to the orientation of the implantable device 30 in patient 16, as well as to the movement of the tracked instrument 61, 61". As the specific orientation of the implantable device 30 within patient 16 may not be known, the calibration process can correlate or register the orientation of the implantable device 30 relative to the display and to movement of the tracked instrument 61, 61". This can be accomplished using the localizer 22 in the implantable device 30 and the respective tracking device 20, 20" associated with the respective tracked instrument 61, 61".

Figure 18:
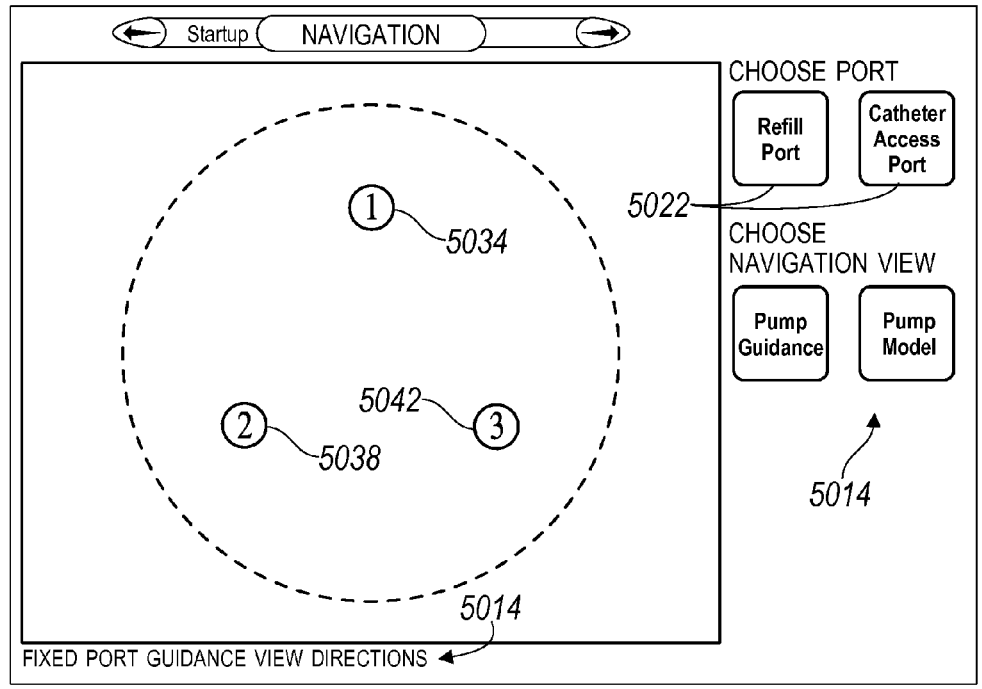
FIG. 18 is an exemplary view of the display device communicating a graphical image associated with a calibration process according to various exemplary embodiments of the present disclosure.

For example, in one exemplary embodiment shown in FIG. 18, the processor system 12 can display a series of three spaced apart calibration points 5034, 5038 and 5042 in a triangular configuration, and prompt the user to direct the tracked instrument 61, 61" to point 5034, then point 5038, and finally point 5042. Upon directing the tracked instrument 61, 61" to each point, the user can provide an indication to the processor system 12 that the tracked instrument 61, 61" is adjacent the respective calibration point. In this manner, based on a known relationship of points 5034-5042, movement of the tracked instrument 61, 61" can be registered to the image area 5010.

As the navigation system 10 is being initialized, the processor system 12 can be configured to determine if the implantable device 30 is out of position such that it is flipped over or inverted inside patient 16 relative to where the user would be attempting to insert the piercing member or needle 4058 into patient 16 towards device 30. The navigation field from the localizer 22 can extend around the implantable device 30 such that the field strength can vary in a predetermined manner relative to a front side 5046 of the implantable device 30 having the target port 32 and an opposite, back side 5050. In this manner, if implantable device 30 is flipped over or inverted, the field strength sensed by the tracking device 20, 20" associated with the tracked instrument 61, 61" can be lower and below a predetermined threshold as compared to the field strength if the front side 5046 was orientated towards the expected anterior or posterior side of the patient, as generally shown in FIG. 1.

Figure 17:
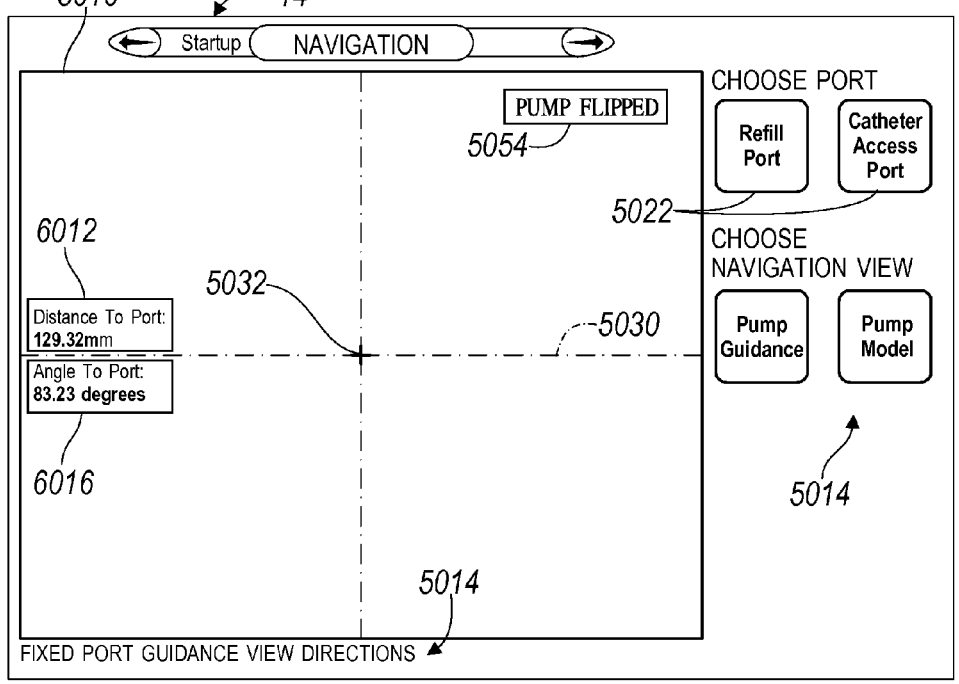
FIG. 17 is an exemplary view of the display device communicating an inverted or flipped condition of the implantable device according to various exemplary embodiments of the present disclosure.

If it is determined that there is a flipped or inverted implantable device condition, the processor system 12 can be configured to display an exemplary graphical indication 5054 in the image area 5010 to alert the user of such a condition upon initialization of the system, as shown in FIG. 17. While FIG. 17 shows graphical indication 5054 as displaying "PUMP FLIPPED", it should be appreciated that various other graphical indications can be used to illustrate or convey to the user that the implantable device 30 is inverted or flipped over. The processor system 12 can be configured to display graphical indication 5054 after initialization of the navigation system 10 and before or after the calibration process is completed. Additionally, the processor system 12 can be configured to remove or not display a graphical representation of the implantable device 30 when the device is flipped over or inverted to aide in drawing the user's attention to the flipped over or inverted status, as also shown in FIG. 17.

The processor system 12 can cooperate with the localizer 22 to provide calibrated guidance zones or areas, such as a first or general guidance zone or area 5064 and a second or detailed guidance zone or area 5068, as shown in FIG. 1. The general guidance area 5064 can include an 8-16 inch (203.2-406.4 mm) diameter or range centered around the target port 32 or implantable device 30, and the detailed guidance area 5068 can include a 4-8 inch (101.6-203.2 mm) diameter or range also centered around the target port 32 or implantable device 30. The navigation system can be configured to determine when the tracked instrument 61, 61" is in one of the areas 5064, 5068, and provide general and detailed guidance information, respectively, as will be discussed in greater detail below. It should be appreciated that the above dimensions for the guidance areas can be varied as may be desired, for example, in connection with different implantable device configurations, localizer configurations, and/or patient sizes.

After the navigation system has been initialized, in a scenario where the implantable device 30 is not inverted or the inverted condition has been diagnosed, the navigation system 10 can prompt the user via display device 14 to select a needle 4058 and input a selected needle length via a keyboard or other input device coupled to the processor system 12 and display device 14. The user can then position the tracked instrument 61, 61" in the general area identified by the palpation and observe the image area 5010 for guidance information. For discussion purposes, a scenario where the user initially positions the tracked instrument 61, 61" in the general guidance area 5064 will be discussed.

Figure 19:
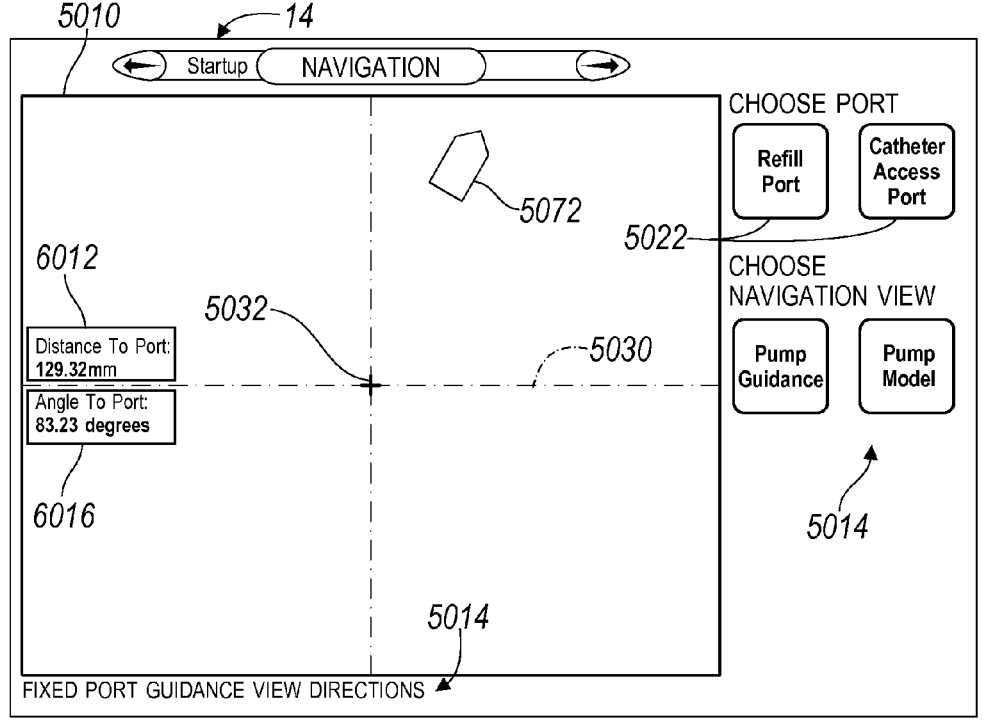
FIG. 19 is an exemplary view of the display device communicating general guidance information according to various exemplary embodiments of the present disclosure.

In this scenario, the processor system 12 is configured to determine that the tracked instrument 61, 61" is within the general guidance area 5064, but outside of area 5068 where specific guidance information can be displayed. General guidance information, such as a directional indicator 5072, can be displayed on the image area 5010 to provide a general indication of a direction to move the tracked instrument 61, 61" toward the target port 32 and thus the area of detailed guidance information 5068. As can be seen in FIG. 19, the directional indicator 5072 can be in the form of an arrow illustrating to the user the general direction to move the tracked instrument 61, 61". However, it should be appreciated that the direction indicator 5072 can be illustrated in various forms sufficient to identify a general direction for guiding or navigating the tracked instrument 61, 61".

Figure 20:
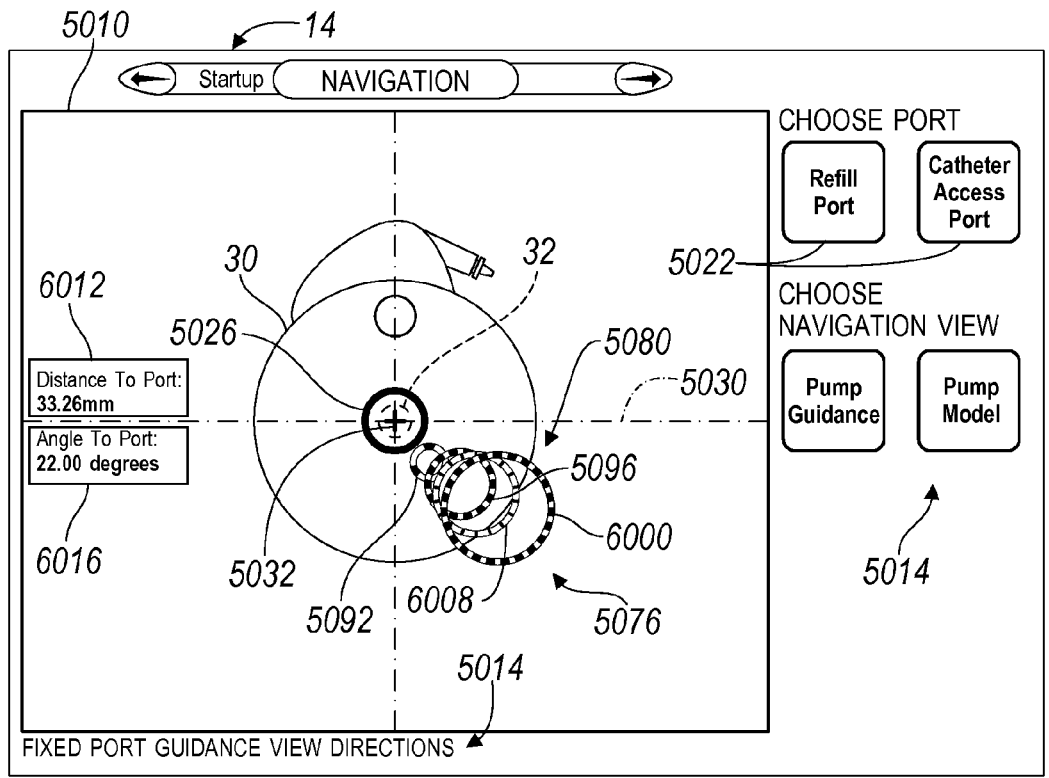
FIG. 20 is an exemplary view of the display device communicating detailed guidance information according to various exemplary embodiments of the present disclosure.
Figure 21:
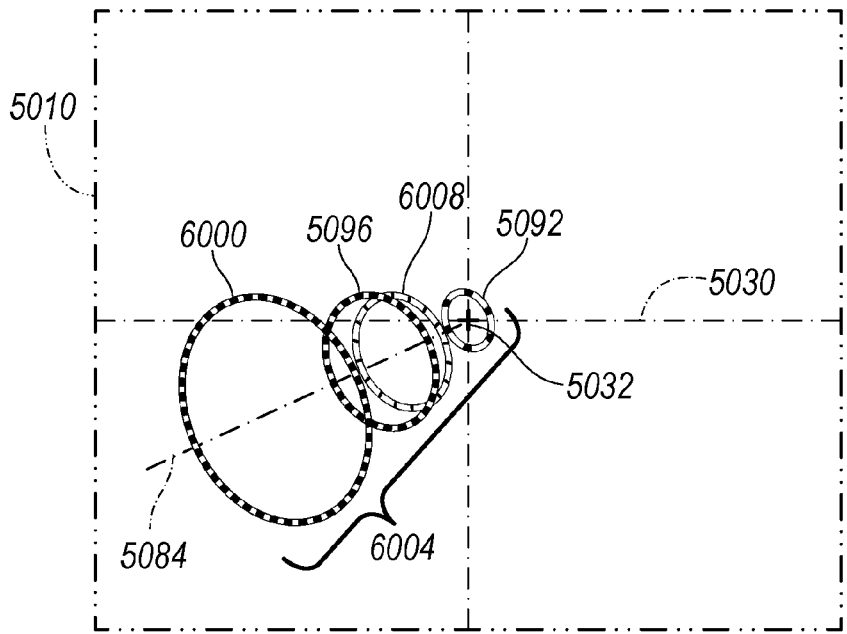
FIG. 21 is another exemplary view of the display device communicating detailed guidance information according to various exemplary embodiments of the present disclosure.

As the user moves the tracked instrument 61, 61" in the general direction of directional indicator 5072, the processor system 12 can be configured to display detailed guidance information 5076 on the image area 5010 when the tracked instrument is positioned in or enters the detailed guidance area 5068, as generally shown for example in FIGS. 20 and 21. It should be appreciated that a user can initially position the tracked instrument 61, 61" in the detailed guidance area 5068 where the detailed guidance information 5076 can be displayed without previously displaying the general guidance information or directional indicator 5072.

With particular reference to FIGS. 20-23, the detailed guidance information 5076 can be displayed in the form of multiple two or three-dimensional guidance rings 5080. The guidance rings 5080 can be a series of two or three-dimensional rings spaced apart a fixed distance. The guidance rings 5080 can be configured to display a location and orientation of the tracked instrument 61, 61" relative to the target port 32, as well as a distance of a distal tip 4059 of the needle 4058 relative to the target port 32, as will be discussed below in greater detail. The guidance rings 5080 can be positioned around a longitudinal axis 5084 and orientated perpendicular to a directional vector of the tracked instrument 61, 61", which can be parallel to the longitudinal axis 5084, as shown in FIG. 21. The guidance rings 5080 can be displayed in the form of three rings—a first ring 5092, a second or middle ring 5096, and a third ring 6000.

Figure 22:
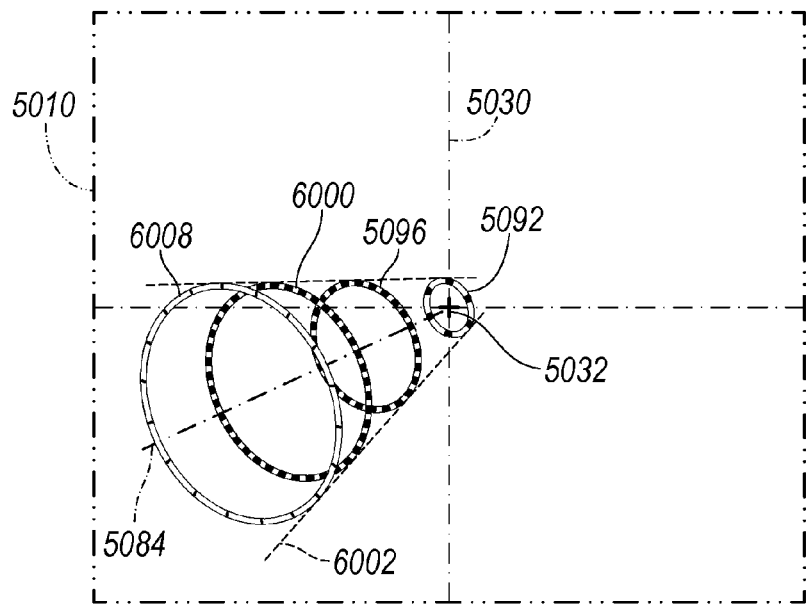
FIG. 22 is another exemplary view of the display device communicating detailed guidance information according to various exemplary embodiments of the present disclosure.

A diameter of each ring can be successively larger from the first ring 5092 to the third ring 5094 so as to form an overall conical shape or form 6002, as shown for example in FIG. 22. Each ring of the guidance rings 5080 can be displayed in a different color on the image area 5010 to facilitate distinguishing the displayed rings from each other. It should be appreciated that while the drawings illustrate patterns associated with the guidance rings 5080, these patterns are for drawing illustration purposes and are used to designate different colors being associated with the rings. Such patterns are not necessary for use in combination with the guidance rings 5080 being displayed with different colors, but may be used in place of colored rings on, for example, a black and white display system. It should also be appreciated that more or less guidance rings can be used to provide the detailed guidance information, as well as different shapes in place of the rings without departing from the spirit or scope of the present disclosure.

The guidance rings 5080 can be displayed spaced apart from each other so as to have an overall length 6004 (FIG. 21) that can be scaled to a distance of the selected needle length, or to a predetermined spaced apart relationship if a needle length has not been selected. In this regard, the first ring 5092 can indicate where the distal tip 4059 of needle 4058 would intersect a point on the implantable device 30 (i.e., a location of the distal tip 4059 relative to the implantable device 30) and the third ring 6000 can indicate the distance or selected needle length 6004 from where the needle would intersect the implantable device 30. The processor system 12 can also be configured to display an additional ring 6008 indicative of a current position of the distal tip 4059 of the selected needle 4058 relative to the selected target port 32 of the implantable device 30. In this regard, when the user places the tracked instrument 61, 61" on or immediately adjacent to the skin of patient 16, the processor system 12 can determine the position of the tracked instrument 61, 61" relative to an entrance of target port 32 and determine if the selected needle length is long enough to extend through a distance from the outer skin surface of patient 16 to the port entrance.

As one of ordinary skill in the art can appreciate, exemplary patient 16 could have various levels of obesity such that while the user can initially attempt to determine an approximate needle length by palpating the area, a verification that the initially selected needle length would reach the implantable device can be beneficial. In this regard, the processor system 12 can be configured to display ring 6008 relative to guidance rings 5080 to provide a visual indication regarding whether the selected needle length is long enough to reach the target port 32. More specifically, when the user places tracked instrument 61, 61" on the skin of patient 16, the ring 6008 can be displayed between the first and third concentric rings 5092, 6000 if the selected needle length is long enough to reach target port 32. If the processor system 12 determines that the selected needle length is not long enough to reach target port 32, then ring 6008 can be placed outside and beyond the third ring 6000 such that it would have a larger diameter than ring 6000, as shown for example in FIG. 22.

Figure 23:
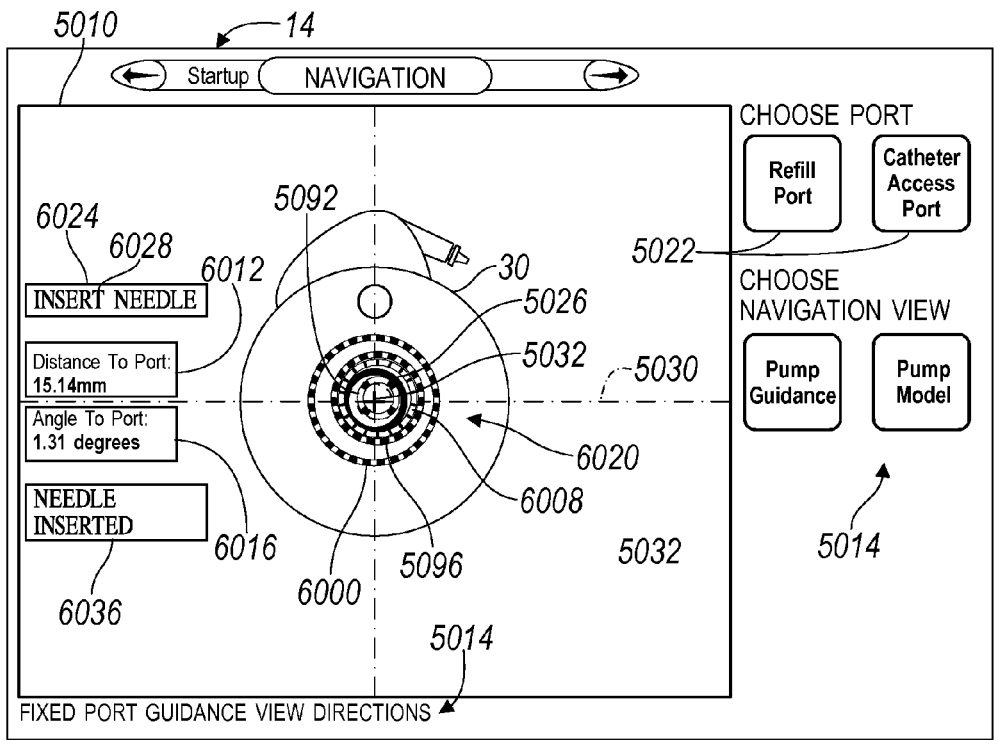
FIG. 23 is another exemplary view of the display device communicating detailed guidance information according to various exemplary embodiments of the present disclosure.

The processor system 12 can be further configured to display a graphical indication 6012 in the form of a numerical distance from the distal tip 4059 of the selected needle 4058 to the entrance of target port 32, as shown for example in FIGS. 20 and 23. Graphical indication 6012 can be displayed when the tracked instrument 61, 61" is in either the general guidance area 5064 or the detailed guidance area 5068, as shown for example in FIGS. 19 and 20, respectively. In addition, the graphical indication 6012 can also be used to provide an additional or alternative indication to the user regarding whether the selected needle length is long enough to reach target port 32. In this regard, the user can position tracked instrument 61, 61" on or immediately adjacent to the skin of patient 16 such that its location and trajectory are aligned with target port 32, as shown in FIG. 23. If the tracked instrument 61, 61" includes the support tool 60, the tool can be placed directly on the skin in the above position. Alternatively, if the tracked instrument 61" is used without the support tool 60, the distal tip 4059 of the needle 4058 can be placed immediately adjacent to the skin in the above position. With either of the tracked instruments 61, 61" in the above position, the user can then read the distance to port numerical indication 6012 to identify a required needle length or to provide another indication that the selected needle length is long enough to reach port 32. For example and with reference to FIG. 23, if the selected needle length is smaller than the displayed distance of 15.14 mm, then the needle 4058 will not be long enough to reach target port 32.

As discussed above, the graphical indication 6012 can be used in combination with ring 6008 or as an alternative to ring 6008. In the exemplary configuration shown in FIGS. 20 and 23, the graphical indication 6012 is shown in combination with ring 6008, where it can be seen that the selected needle length is long enough based on ring 6008 being smaller than third ring 6000 and between the first and third rings 5092, 6000. If the selected needle length is determined not to be long enough, as shown in FIG. 22, then the user can select a longer needle, enter the newly selected needle length, and the navigation system can display ring 6008 relative to the guidance rings 5080 to provide the visual indication regarding whether the newly selected needle length will be long enough to reach target port 32.

In an alternative configuration, the processor system 12 can be operable to automatically determine a required length of the needle 4058 to reach the target port 32 without first prompting the user to select a needle 4058 and input an initial needle length, as discussed above. In this regard, the user can place the tracked instrument 61, 61" on the skin of the patient and align the location and trajectory of the tracked instrument 61, 61" with the target port, as will be described in more detail below. Once aligned, the processor system 12 can automatically determine the required needle length to reach target port 32 and can be operable to cause the display device 14 to graphically render a required needle length and/or product code or descriptor indicative of a certain needle 4058 with the required length to be selected by the user.

The processor system 12 can be operable to display ring 6008 relative to the first and third rings 5092, 6000 once the processor system 12 has determined the required needle length in this alternative configuration. Additionally, the processor system 12 can maintain a database including a list of preconfigured needles 4058 having various lengths and can be operable to select a specific needle from the list upon determining the required needle length as described above. In this regard, if the determined needle length is between two available needle length configurations stored in the list, the processor system can be operable to select the needle 4058 with the longer length to be communicated to the display device 14 as described above.

With the tracked instrument 61, 61" positioned in the detailed guidance area 5068 such that the detailed guidance information 5076 is displayed, the user can align an insertion trajectory of the tracked instrument 61, 61" with the axis X of target port 32. If the tracked instrument 61 is used, the trackable support tool 60 can be manipulated about an outer surface of patient 16 such that the insertion trajectory or axis X" of support tool 60 aligns with axis X of target port 32. On the other hand, if the trackable supply assembly 50 with removably coupled tracking device 20" is being used without the support tool 60, the insertion trajectory or axis X' of the needle 4058 can be aligned with the axis X of target port 32.

The processor system 12 can be configured to display a trajectory or angular relationship of the longitudinal axis 5084 of guidance rings 5080 relative to the axis X of target port 32, as shown for example in FIGS. 20 and 23. When the insertion trajectory or axis (X' or X") of tracked instrument 61, 61" is not in alignment with the axis X of target port 32 (which is parallel to the view direction or perpendicular to the two-dimensional image view of FIGS. 20-23), the guidance rings 5092-6000, as well as ring 6008 (if a needle length has been selected), can be shown in a non-concentric relationship relative to an axis parallel to axis X of target port 32, as shown in FIGS. 20-22. Such non-concentric illustration of guidance rings 5092-6000 can indicate to the user that the insertion trajectory of the tracked instrument 61, 61" and axis X of target port 32 are not aligned, as shown for example in FIG. 20. In addition, the processor system 12 can be configured to also display a graphical indication 6016 indicative of an angular relationship between the axis of the tracked instrument 61, 61" and axis X of target port 32. Graphical indication 6016 can, for example, include a numerical value of an angular offset between axis X of target port 32 and the axis or insertion trajectory of tracked instrument 61, 61", such as the "ANGLE TO PORT: 22.00 degrees" indication illustrated in FIG. 20.

Using the guidance rings 5080 and/or the graphical indication 6016, the user can manipulate the orientation of the trajectory of tracked instrument 61, 61" such that the longitudinal axis or insertion trajectory of tracked instrument 61, 61" (i.e., X' or X"), and thus the longitudinal axis 5084 of guidance rings 5080, are parallel to axis X of target port 32. In this manner, the user can observe the display of guidance rings 5080 and manipulate the tracked instrument 61, 61" such that guidance rings 5080 form a concentric or bull's eye pattern 6020 about an axis parallel axis X of target port 32, as shown in FIG. 23. The concentric pattern 6020 can provide a visual indication that the respective axis of tracked instrument 61, 61" is in parallel alignment with axis X of target port 32. While FIG. 23 illustrates guidance rings 5080 in a concentric pattern over or surrounding the target location 5032, it should be appreciated that the trajectory of tracked instrument 61, 61" can be aligned with axis X of target port 32 when in a location not over or away from target location 5032. It should also be appreciated that longitudinal axis 5084 is shown for discussion purposes and is not required to display the trajectory of tracked instrument 61, 61".

As discussed above, the processor system 12 can be configured to display a location of tracked instrument 61, 61" relative to target port 32 of the implantable device 30. In this regard, the user can move or navigate tracked instrument 61, 61" relative to the skin of patient 16 so as to place the first ring 5092 of the guidance rings 5080 over the graphical rendering of cross-hair target location 5032, as shown in FIG. 23. Having the first ring 5092 surrounding target location 5032 of target port 32 can provide visual confirmation to the user that at least a distal end of the selected needle 4058 of the tracked instrument 61, 61" is over or above target port 32. If the trajectory of tracked instrument 61, 61" has already been aligned with axis X of target port 32, then the guidance rings 5080 can be concentric about an axis parallel to axis X of target port 32 and surrounding target location 5032, as shown for example in FIG. 23.

However, it should be appreciated that the location of tracked instrument 61, 61" can be positioned over target port 32 without first aligning the trajectory of tracked instrument 61, 61" with axis X of target port 32, as shown for example in FIG. 21. In this scenario, the first ring 5092 can be positioned over target location 5032, but the remaining guidance rings 5096 and 6000 will not be concentrically aligned with first ring 5092, thus indicating that the trajectory of the tracked instrument 61, 61" and axis X of port 32 are not aligned. In this case, the trajectory of the tracked instrument 61, 61" can then be aligned with axis X of target port 32 such that the guidance rings 5080 can be concentrically located around target location 5032, as shown in FIG. 23.

Once both the location and the trajectory of the tracked instrument 61, 61" are aligned with target port 32, the processor system 12 can be configured to provide a graphical indication 6024 in image area 5070 confirming the location and trajectory of tracked instrument 61, 61" are aligned with target port 32 such that the needle 4058 can then be inserted into target port 32. In one aspect of the present teachings, graphical indication 6024 can be in the form of a prompt 6028 on image area 5070 that displays "INSERT NEEDLE" as shown in FIG. 23.

With reference to FIGS. 1, 20-21 and 23, insertion of needle 4058 into target port 32 will now be discussed in greater detail. With reference to tracked instrument 61" having the trackable supply assembly 50 with removably coupled tracking device 20", once the trajectory and location of tracked instrument 61" are aligned as discussed above, the needle 4058 can be inserted into patient 16 and into target port 32. As the needle 4058 is being inserted, a distance from the distal tip 4059 of the needle 4058 to the target port 32 continually decreases until distal tip 4059 reaches and enters target port 32. During such insertion, the processor system 12 can be configured to track a position of distal tip 4059 relative to target port 32 when the tracked instrument 61" is utilized, as the tracking device 20" moves with needle 4058 during insertion of the needle. In this manner, ring 6008 can move along the longitudinal axis 5084 of guidance rings 5080 during insertion of needle 4058 from an initial position where the distal tip 4059 is adjacent the skin of patient 16 towards the first ring 5092, which is indicative of a position within patient 16 at which the distal tip 4059 of needle 4058 can intersect target port 32.

As ring 6008 moves towards first ring 5092, the diameter of ring 6008 can progressively decrease proportionally to the conical form 6002 of guidance rings 5080 such that as ring 6008 reaches first ring 5092, it can have the same or substantially the same diameter as first ring 5092. In this manner, when the guidance rings 5080 are concentrically aligned over target location 5032 as shown in FIG. 23, the progressively decreasing diameter of ring 6008 during the needle insertion process can provide a visual indication of the proximity to the entrance of target port 32. When ring 6002 reaches the same depth as first ring 5092, which can be signified by having the same diameter in a concentric pattern of the rings, the distal tip 4059 of needle 4058 can be at the entrance to target port 32.

If the support tool 60 is used with the non-trackable supply assembly 50 (i.e., without the tracking device 20" coupled thereto), the navigation system 10 can be configured to also display ring 6008 relative to the guidance rings 5080 to provide the above-discussed visual feedback regarding whether the selected needle length is long enough to reach target port 32. However, as the tracking device 20 in support tool 60 can be fixed relative to the tool, it does not move in this configuration along with the needle 4058 when it is being inserted. In this aspect of the present teachings, ring 6008 can remain stationary during insertion of needle 4058.

The processor system 12 can also be configured to provide feedback that the needle 4058 has been successfully inserted into target port 32. In one aspect of the present teachings, the implantable device 30 can include a sensor, such as a transducer 6032, associated with target port 32 such that when the distal tip 4059 of needle 4058 is received therein, a graphical indicator 6036 can be displayed to provide confirmation that needle 4058 has been inserted into target port 32. The transducer 6032 can also be configured to not only provide confirmation that the target port 32 has been reached by needle 4058, but also that the needle 4058 has been inserted into target port 32 to a predetermined depth sufficient for delivery of the functional fluid to reservoir 34. A wireless link can be established between the implantable device 30 and the processor system 12 to facilitate communication therebetween.

Figure 24:
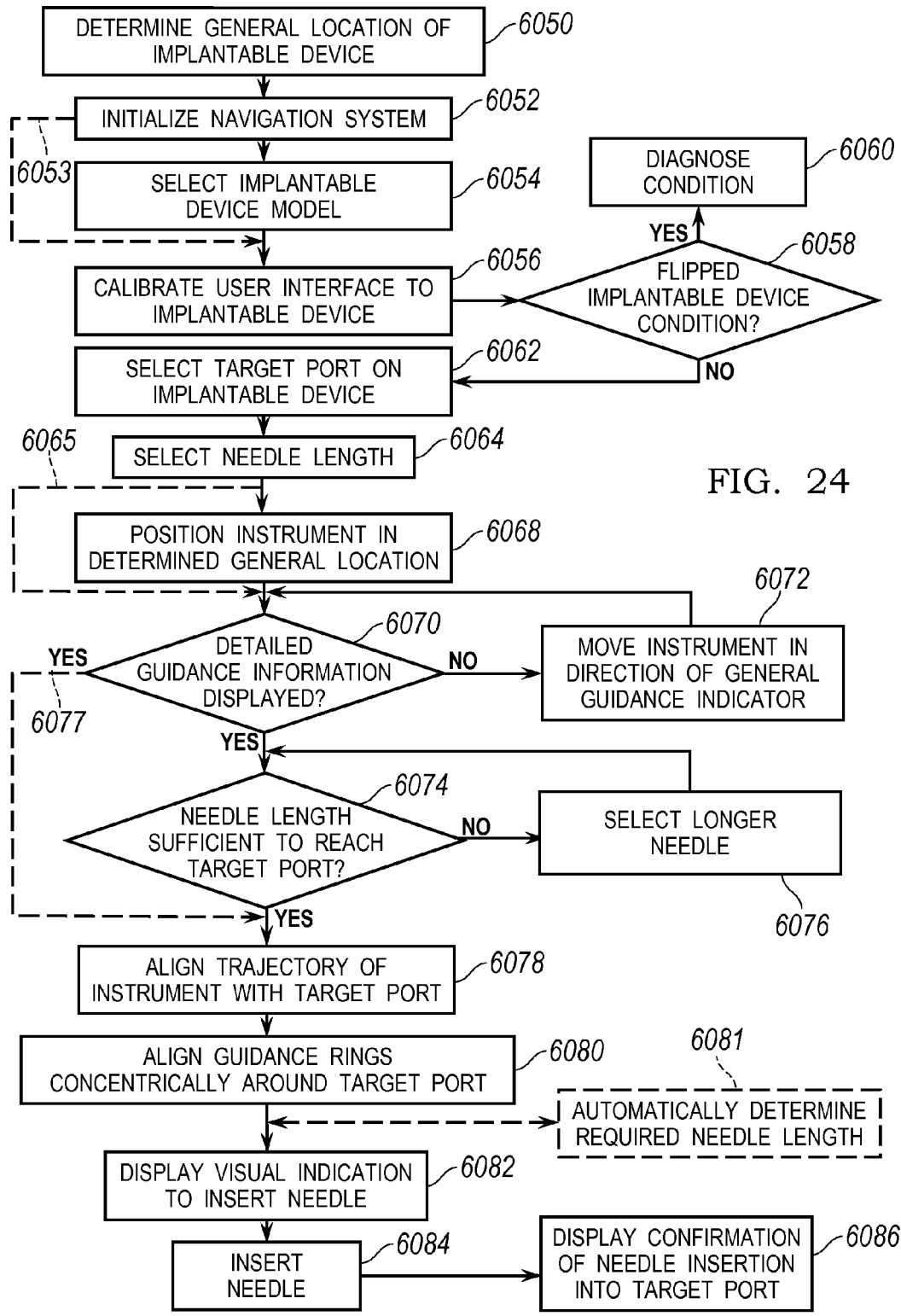
FIG. 24 is an illustration of an exemplary procedure according to various exemplary embodiments of the present disclosure.

Turning now to FIG. 24, a logic block diagram illustrating an exemplary method or procedure for utilizing the navigation system 10 having the implantable device 30 and tracked instrument 61, 61" is illustrated in further detail. As generally discussed above in connection with the system for displaying guidance information, the procedure can include palpating patient 16 at block 6050 to determine a general location of the implantable device 30, as well as a general indication of a needle length than can be required to reach the implantable device 30. The navigation system 10 can be initialized at block 6052 and then the user can proceed to select the implantable device model at block 6054 that is associated with patient 16 from a preconfigured menu or database associated with processor system 12. It should be appreciated that while FIG. 24 illustrates initializing the navigation system 10 after determining the general location of implantable device 30, these procedures could be carried out concurrently or in a reverse order. In addition, the navigation system can be initialized via data communicated via the telemetry system and the implantable device model associated with patient 16 can be automatically determined by the data sent via the telemetry system. In this alternative configuration, the procedure can continue along phantom line 6053 from block 6052 to block 6056.

Upon selection of the implantable device model (or receiving data identifying the model), the procedure can continue to the calibration process described above and referenced at block 6056. Upon completing the calibration process, the navigation system can be configured to identify whether the flipped pump condition exists at block 6058. It should again be appreciated that while the flipped pump condition determination is illustrated after the calibration process block 6056, the navigation system 10 can be configured to determine whether the flipped pump condition exists concurrently with or before the calibration process. If the flipped pump condition is identified, the procedure can continue with diagnosing the flipped pump condition at block 6060. If the flipped pump condition is not identified by the navigation system 10, then the procedure can continue to block 6062 where the user can be prompted to select the target port, such as port 32 discussed above, if the selected implantable device model includes more than one port configured to receive a functional fluid or the like. It should be appreciated that it may not be necessary to select the target port if, for example, the selected implantable device model includes only one applicable port for receiving the functional fluid.

The procedure can continue to block 6064 where the needle length can be selected and the selected length communicated to the processor system 12. The user can be requested to enter the needle length via the prompt displayed in the image area 5010, as discussed above. With the needle length selected, the procedure can continue to block 6068 where the tracked instrument 61, 61" can be placed on or adjacent to the skin of patient 16 in the general area determined in block 6050. Upon positioning the tracked instrument 61, 61" in this area, the user can observe the image area 5010 for guidance information to align and locate the tracked instrument relative to the target port 32 of the implantable device 30. In an alternative configuration where the processor system 12 is operable to automatically select the required needle length once the tracked instrument 61, 61" is aligned with the target port, the procedure can bypass block 6064 and continue from block 6062 along phantom line 6065 to block 6070.

Depending on where the tracked instrument is initially positioned relative to the general and detailed guidance areas, the user may observe general directional indicator 5072 or detailed guidance information 5076 if the tracked instrument 61, 61" is positioned in detailed guidance area 5068. Additionally, it is possible that neither the general or detailed guidance information can be displayed if the tracked instrument 61, 61" is initially positioned outside the general guidance area 5064. If general guidance information is displayed at decision block 6070, such as the directional indicator 5072, the user can move the tracked instrument in the direction indicated by directional indicator 5072 until the detailed guidance information 5076 is displayed, as noted in block 6072.

With the detailed guidance information being displayed, the procedure can continue to decision block 6074 where the user can determine if the selected needle length is long enough to reach the target port 32. As discussed above, the user can determine if the selected needle length is of sufficient length to reach target port 32 through use of ring 6008 and/or graphical indicator 6012, and if not, select a longer needle as noted in block 6076. In addition, as also discussed above, it should be appreciated that the determination regarding the selected needle length can be performed at various times throughout the procedure, including after the tracked instrument 61, 61" has been located and aligned relative to target port 32.

The procedure can continue to block 6078 where the trajectory of the tracked instrument 61, 61" can be aligned with axis X of target port 32. With the trajectory aligned, the tracked instrument 61, 61" can be translated until first ring 5092 is located over target port 32 such that the graphical representation of target location 5032 is encompassed by first ring 5092, as referenced in block 6080.

In the alternative configuration where the processor system 12 is operable to automatically determine the required needle length to reach the target port 32, the procedure can bypass blocks 6074 and 6076 and continue from block 6070 to block 6078 along phantom line 6077. In this configuration, the procedure can continue from block 6080 to block 6081 where the processor can automatically determine a required needle length for the tracked instrument 61 or 61" to reach target port 32.

The procedure can then continue to block 6082 where graphical indicator 6024 can be displayed to instruct the user to insert needle 4058 into target port 32. The needle 4058 can then be inserted at block 6084 and a confirmation can be displayed at block 6086 indicating that the needle 4058 has been received in target port 32. At this point, the reservoir can be filled with the functional fluid and the needle 4058 can then be removed from the target port 32.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A system for determining a location of a trackable instrument with a receiving coil array, comprising:
   a trackable instrument;
   a tracking array associated with the trackable instrument, having:
      a plurality of tracking portions;
      wherein each tracking portion of the plurality of tracking portions is positioned at vertices of a geometric shape separately and spaced apart from each of the other tracking portions to form the tracking array;
      wherein the geometric shape is a tetrahedron and the plurality of tracking portions includes four tracking portions, wherein each tracking portion is spaced about eight millimeters to about 15 millimeters apart from each other tracking portion;
      wherein each tracking portion is operable to sense a field to determine position information and orientation information;
   an implantable medical device having a power source;
   a localizer having coils of conductive material and configured to emit an electromagnetic field when powered by the power source fixed within the implanted medical device operable to emit a field to be sensed by the tracking array; and
   a display separate from the trackable instrument and operable to display a location information of the trackable instrument based on the emitted field from the localizer that is sensed by the tracking array, wherein the location information includes a graphical display representing a port of the implantable medical device and a direction indicator relative to the port displayed as a plurality of rings;
   wherein the plurality of rings on the display illustrate detailed guidance information including
   three-dimension position and orientation of the trackable instrument.

2. The system of claim 1, wherein each of the four tracking portions has three conductive coils for a total of 12 conductive coils in the tracking array.

3. The system of claim 2, wherein each of the four tracking portions has the three conductive coils wound substantially around a single origin.

4. The system of claim 3, wherein the three conductive coils is at least one of each coil wound separately, set adjacent to one another, or set orthogonal to each other.

5. The system of claim 1, wherein the trackable instrument includes a fillable container having a piercing member extending from the fillable container;
   wherein the trackable instrument is integrated with the fillable container, the piercing member, or combinations thereof to move substantially with the fillable container and the piercing member.

6. The system of claim 1, further comprising:
   a guide support having a passage and including the tracking array as the trackable instrument; and
   a fillable container operable to be guided with the guide support at least in part by being positioned through the passage of the guide support.

7. The system of claim 6, wherein the fillable container is moveable separately from the guide support and positioned in the guide support when the guide support is in the selected location.

8. The system of claim 2,
   wherein each of the four conductive coil groups are spaced apart from one another to sense the field of different positions relative to the trackable instrument.

9. The system of claim 1, wherein the displayed positions the plurality of guidance rings relative to each other are determined by a processor configured to illustrate whether the length of the selected piercing member is long enough to reach the implantable medical device.

10. A system for receiving a functional material and delivering the received functional material to a patient, comprising:
an implantable medical device configured to receive the functional material that is operable to be delivered to the implantable medical device with a delivery system;
a navigation processor operable to process a signal based on a field sensed by tracking portions of the delivery system to determine a location of the delivery system;
a localizer configured to generate the field and included with the implantable medical device, wherein the localizer included with the implantable medical device is fixed within the implantable medical device and includes at least three coils, wherein each of the at least three coils includes a first coil layer of a first number of turns and a second coil layer of a second number of turns separated by a plane defined by an isolation layer, wherein the first coil layer is positioned at a first side of the isolation layer and the second coil layer is positioned at an opposite second side of the isolation layer;
a localizer tuning capacitor connected to at least one coil of the at least three coils of the localizer to tune a driving signal through at least one coil of the at least three coils;
a telemetry tuning capacitor separate from the localizer tuning capacitor and connected to at least one coil of the at least three coils of the localizer to tune the driving signal through at least one coil of the at least three coils;
a tuning control to switch an incoming current to oscillate through both the telemetry tuning capacitor and the localizer tuning capacitor or only the telemetry tuning capacitor and at least one of the coils of the at least three coils to selectively tune the driving signal for one of telemetry or localizing;
a single power source configured to power the implantable medical device to deliver the functional material and the localizer; and
a power management module configured to conserve power of the single power source by selectively powering at least one of the implantable medical device to deliver the functional material and the localizer based on a set of instructions.

11. The system of claim 5, wherein the tracking array is coupled directly to the fillable container at a known location relative to a distal tip of the piercing member;
wherein the tracking array is keyed to the fillable container such that the tracking array is at a known orientation relative to the fillable container when attached thereto.

12. The system of claim 10, further comprising:
a display device operable to display location information regarding the delivery system relative to the implantable medical device including at least detailed guidance information including at least a guidance ring illustrating a location of the delivery system displayed relative to a graphical display representing the port.

13. The system of claim 10 further comprising the tracking portions and the delivery system, wherein the tracking portions are positioned substantially in a selected geometric shape that has a volume of about 250 millimeters cubed, where each of the tracking portions includes a conductive material, three individual coils that are aligned on an axis substantially orthogonal to one another, and spaced apart from one another.

14. The system of claim 13, wherein each tracking portion of the tracking portions is about 12.5 mm apart from an adjacent one of the tracking portions.

15. The system of claim 13, wherein each of the three individual coils of each of the tracking portions is wound annularly around a single center point and substantially in a circle around the center point and each of the three individual coils are wrapped substantially circularly around the axis in which they are aligned.

16. The system of claim 10, wherein each first coil layer of each coil of the at least three coils of the localizer includes the first number of turns of about 10 turns to about 100 turns.

17. The system of claim 10, wherein the first number of turns is about 38 turns to about 42 turns.

18. The system of claim 10, wherein a thickness of a trace or wire of each of the first coil layer is about 0.025 mm to about 0.25 mm.

19. The system of claim 10, wherein a thickness of a trace or wire of each of the first coil layer is about 0.0483 mm to about 0.203 mm.

20. The system of claim 10, wherein the at least three coils of the localizer emit the only field for determination of a location of the plurality of tracking portions relative to the implantable medical device and are positioned in the implantable medical device to allow for a compact and contained navigation system.

21. The system of claim 10, wherein at least one coil of the at least three coils is oval shaped, lima bean shaped, or cylindrical shaped.

22. A system for determining a location of a trackable instrument with a receiving coil array, comprising:
twelve conductive coils arranged in the receiving coil array;
four conductive coil groups where each of the four conductive coil groups has three of the twelve conductive coils;
a localizer positioned in an implanted medical device operable to emit a field to be sensed by each of the twelve conductive coils; and
a delivery system having a supply assembly that includes a container and a piercing member that extends from the container;
a support member having a first surface spaced from and opposed to a second surface and a throughbore extending between and through the first surface and the second surface, wherein the support member is configured to selectively and removably engage the delivery system, wherein the piercing member is configured to selectively and removably received in the throughbore;
wherein each of the four conductive coil groups is positioned spaced apart about eight millimeters to about 15 millimeters at vertices of a tetrahedron to define a volume of about 200 millimeters cubed to about 300 millimeters cubed;
wherein fields sensed at each of the four conductive coil groups is operable to determine position information and orientation information for each of the coil groups relative to the localizer;
wherein the support member houses the four conductive coil groups of the receiving coil array for sensing the field from the localizer;
wherein extending from the first surface of the support member further includes an upper three dimensionally contoured nesting surface that conforms to a corresponding three dimensionally contoured surface of the supply assembly, the corresponding surface of the supply assembly nests against the upper three dimensionally contoured nesting surface to support the supply assembly such that a supply axis remains substantially fixed relative to the receiving coil array;
wherein the piercing member extends through the throughbore and into the implanted medical device;

wherein a lower nesting surface extends from the upper nesting surface and towards the second surface;

wherein the container nests against and abuts the entire upper three dimensionally contoured nesting surface and the piercing member nests within and abuts the entire lower nesting surface when the container nests against the upper three dimensionally contoured nesting surface;

wherein the container when nested within the upper nesting surface is at least partially below the upper surface of the support member.

23. The system of claim 22, wherein the implanted medical device includes a reservoir operable to hold a functional fluid:

a pump operable to pump the functional fluid from the implanted medical device to a patient; and a port operable to provide filling access to the reservoir from an exterior of the implanted medical device.

24. The system of claim 23, further comprising:

the delivery system operable to deliver the functional fluid to the reservoir in the implanted medical device;

wherein the receiving coil array is associated with the delivery system.

25. The system of claim 24, wherein each of the four conductive coil groups is about 10 millimeters to about 15 millimeters apart from one another;

wherein one of the coil groups is placed at a vertex of a shape defining a tetrahedron the vertices.

26. The system of claim 25, further comprising:

a display device operable to display a determined position information and orientation information of the delivery system;

wherein a delivery system is operable to be moved relative to the implanted medical device and the determined position information and orientation information is operable to be displayed on the display device for viewing by a user.

27. The system of claim 22, wherein the coils in each of the four conductive coil groups is operable to sense the field operable to allow determination of location information of each of the four conductive coil groups of the receiving coil array relative to the localizer.

28. The system of claim 27, wherein the support member includes an opening that can receive the supply assembly, wherein the opening extends from an outer perimeter of the support member to allow at least the piercing member to move through the outer perimeter into the opening and into the throughbore.

29. The system of claim 28, further comprising:

a removable member to be positioned in the opening;

wherein the removable member at least partially defines at least one of the upper nesting surface or the lower nesting surface.

* * * * *